US007150764B2

(12) United States Patent
Plos et al.

(10) Patent No.: US 7,150,764 B2
(45) Date of Patent: Dec. 19, 2006

(54) COMPOSITION FOR DYEING A HUMAN KERATIN MATERIAL, COMPRISING AT LEAST ONE FLUORESCENT DYE AND AT LEAST ONE INSOLUBLE CONDITIONING AGENT, PROCESS THEREOF, USE THEREOF, AND DEVICES THEREOF

(75) Inventors: Grégory Plos, Paris (FR); Henri Samain, Bievres (FR)

(73) Assignee: L'Oreal S.A., Paris (FR)

( * ) Notice: Subject to any disclaimer, the term of this patent is extended or adjusted under 35 U.S.C. 154(b) by 167 days.

(21) Appl. No.: 10/814,337

(22) Filed: Apr. 1, 2004

(65) Prior Publication Data
US 2005/0076457 A1 Apr. 14, 2005

Related U.S. Application Data

(60) Provisional application No. 60/468,063, filed on May 6, 2003.

(30) Foreign Application Priority Data
Apr. 1, 2003 (FR) .................................. 03 04021

(51) Int. Cl.
*A61K 7/13* (2006.01)
(52) U.S. Cl. ...................... 8/405; 8/406; 8/407; 8/410; 8/411; 8/421; 8/521; 8/648; 132/202; 132/208
(58) Field of Classification Search ............. 8/405, 8/406, 407, 410, 411, 421, 521, 648; 132/202, 132/208
See application file for complete search history.

(56) References Cited

U.S. PATENT DOCUMENTS

| 2,261,002 | A | 10/1941 | Ritter |
| 2,271,378 | A | 1/1942 | Searle |
| 2,273,780 | A | 2/1942 | Ditmar |
| 2,375,853 | A | 5/1945 | Kirby et al. |
| 2,388,614 | A | 11/1945 | Kirby et al. |
| 2,454,547 | A | 11/1948 | Bock et al. |
| 2,798,053 | A | 7/1957 | Brown |
| 2,851,424 | A | 9/1958 | Switzer et al. |
| 2,923,692 | A | 2/1960 | Ackerman et al. |
| 2,961,347 | A | 11/1960 | Floyd |
| 2,979,465 | A | 4/1961 | Parran et al. |
| 3,014,041 | A | 12/1961 | Hausermann et al. |
| 3,206,462 | A | 9/1965 | McCarty |
| 3,227,615 | A | 1/1966 | Korden |
| 3,472,840 | A | 10/1969 | Stone et al. |
| 3,632,559 | A | 1/1972 | Matter et al. |
| 3,639,127 | A | 2/1972 | Brooker et al. |
| 3,658,985 | A | 4/1972 | Olson, Jr. et al. |
| 3,856,550 | A | 12/1974 | Bens et al. |
| 3,874,870 | A | 4/1975 | Green et al. |
| 3,910,862 | A | 10/1975 | Barabas et al. |
| 3,912,808 | A | 10/1975 | Sokol |
| 3,915,921 | A | 10/1975 | Schlatzer, Jr. |
| 3,917,817 | A | 11/1975 | Vanlerberghe et al. |
| 3,929,990 | A | 12/1975 | Green et al. |
| 3,966,904 | A | 6/1976 | Green et al. |
| 3,986,825 | A | 10/1976 | Sokol |
| 4,001,432 | A | 1/1977 | Green et al. |
| 4,005,193 | A | 1/1977 | Green et al. |
| 4,013,787 | A | 3/1977 | Varlerberghe et al. |
| 4,025,617 | A | 5/1977 | Green et al. |
| 4,025,627 | A | 5/1977 | Green et al. |
| 4,025,653 | A | 5/1977 | Green et al. |
| 4,026,945 | A | 5/1977 | Green et al. |
| 4,027,020 | A | 5/1977 | Green et al. |
| 4,031,307 | A | 6/1977 | DeMartino et al. |
| 4,075,136 | A | 2/1978 | Schaper |
| 4,131,576 | A | 12/1978 | Iovine et al. |
| 4,157,388 | A | 6/1979 | Christiansen |
| 4,165,367 | A | 8/1979 | Chakrabarti |
| 4,166,894 | A | 9/1979 | Schaper |
| 4,172,887 | A | 10/1979 | Vanlerberghe et al. |
| 4,185,087 | A | 1/1980 | Morlino |
| 4,189,468 | A | 2/1980 | Vanlerberghe et al. |
| 4,197,865 | A | 4/1980 | Jacquet et al. |
| 4,217,914 | A | 8/1980 | Jacquet et al. |
| 4,223,009 | A | 9/1980 | Chakrabarti |
| 4,237,243 | A | 12/1980 | Quack et al. |
| 4,240,450 | A | 12/1980 | Grollier et al. |
| 4,256,458 | A | 3/1981 | Degen et al. |
| 4,277,581 | A | 7/1981 | Vanlerberghe et al. |
| 4,381,919 | A | 5/1983 | Jacquet et al. |
| 4,422,853 | A | 12/1983 | Jacquet et al. |

(Continued)

FOREIGN PATENT DOCUMENTS

AT 302 534 10/1972

(Continued)

OTHER PUBLICATIONS

CAS Abstract for JP 2000-136340—Chemical Abstracts Service; Database Accession No. 2000: 317079; XP-002269220, JP 2000136340 (Pentel Co., Ltd.), May 16, 2000.

(Continued)

*Primary Examiner*—Eisa Elhilo
(74) *Attorney, Agent, or Firm*—Finnegan, Henderson, Farabow, Garrett & Dunner LLP

(57) ABSTRACT

A composition comprising at least one fluorescent dye and at least one insoluble conditioning agent; and processes and multicompartment kits comprising the composition. This disclosure also relates to the use of this composition for dyeing a human keratin material, and, for example, artificially dyed or pigmented hair and/or dark skin, with a lightening effect.

51 Claims, No Drawings

U.S. PATENT DOCUMENTS

| | | |
|---|---|---|
| 4,445,521 A | 5/1984 | Grollier et al. |
| 4,509,949 A | 4/1985 | Huang et al. |
| 4,591,160 A | 5/1986 | Grollier |
| 4,608,250 A | 8/1986 | Jacquet et al. |
| 4,693,935 A | 9/1987 | Mazurek |
| 4,702,906 A | 10/1987 | Jacquet et al. |
| 4,719,099 A | 1/1988 | Grollier et al. |
| 4,719,282 A | 1/1988 | Nadolsky et al. |
| 4,728,571 A | 3/1988 | Clemens et al. |
| 4,761,273 A | 8/1988 | Grollier et al. |
| 4,781,724 A | 11/1988 | Wajaroff et al. |
| 4,823,985 A | 4/1989 | Grollier et al. |
| 4,839,166 A | 6/1989 | Grollier et al. |
| 4,948,579 A | 8/1990 | Jacquet et al. |
| 4,961,925 A | 10/1990 | Tsujino et al. |
| 4,972,037 A | 11/1990 | Garbe et al. |
| 4,996,059 A | 2/1991 | Grollier et al. |
| 5,009,880 A | 4/1991 | Grollier et al. |
| 5,057,311 A | 10/1991 | Hanazawa et al. |
| 5,089,252 A | 2/1992 | Grollier et al. |
| 5,139,037 A | 8/1992 | Grollier et al. |
| 5,188,639 A | 2/1993 | Schultz et al. |
| 5,196,189 A | 3/1993 | Jacquet et al. |
| 5,275,808 A | 1/1994 | De Groot et al. |
| 5,356,438 A | 10/1994 | Kim et al. |
| 5,445,655 A | 8/1995 | Kuhn et al. |
| 5,635,461 A | 6/1997 | Onitsuka et al. |
| 5,708,151 A | 1/1998 | Möckli |
| 5,733,343 A | 3/1998 | Mockli |
| 5,744,127 A * | 4/1998 | Giuseppe et al. ............. 424/59 |
| 5,792,221 A | 8/1998 | Lagrange et al. |
| 5,830,446 A | 11/1998 | Berthiaume et al. |
| 5,833,997 A | 11/1998 | Mahieu et al. |
| 5,853,708 A * | 12/1998 | Cauwet et al. ........... 424/70.22 |
| 5,873,494 A | 2/1999 | Dallas, Jr. |
| 5,958,392 A | 9/1999 | Grollier et al. |
| 5,962,522 A | 10/1999 | Wacher et al. |
| 6,106,577 A | 8/2000 | Audousset et al. |
| 6,120,780 A | 9/2000 | Dupuis et al. |
| 6,180,666 B1 | 1/2001 | Wacher et al. |
| 6,260,556 B1 | 7/2001 | Legrand et al. |
| 6,375,958 B1 | 4/2002 | Cauwet et al. |
| 6,391,062 B1 * | 5/2002 | Vandenbossche et al. ...... 8/405 |
| 6,436,151 B1 | 8/2002 | Cottard et al. |
| 6,436,153 B1 * | 8/2002 | Rondeau ........................ 8/426 |
| 6,475,248 B1 | 11/2002 | Ohashi et al. |
| 6,570,019 B1 | 5/2003 | Pasquier et al. |
| 6,576,024 B1 | 6/2003 | Lang et al. |
| 6,592,630 B1 | 7/2003 | Matsunaga et al. |
| 6,616,709 B1 | 9/2003 | Ohashi et al. |
| 6,712,861 B1 | 3/2004 | Rondeau |
| 2001/0010812 A1 | 8/2001 | Chevalier et al. |
| 2001/0023514 A1 | 9/2001 | Cottard et al. |
| 2001/0023515 A1 | 9/2001 | Cottard et al. |
| 2001/0031270 A1 | 10/2001 | Douin et al. |
| 2001/0034914 A1* | 11/2001 | Saunier et al. .................. 8/405 |
| 2001/0054206 A1* | 12/2001 | Matsunaga et al. ............ 8/405 |
| 2001/0055580 A1 | 12/2001 | Belli et al. |
| 2002/0004956 A1 | 1/2002 | Rondeau |
| 2002/0012681 A1 | 1/2002 | George et al. |
| 2002/0026676 A1 | 3/2002 | Ohashi et al. |
| 2002/0046431 A1 | 4/2002 | Laurent et al. |
| 2002/0046432 A1 | 4/2002 | Rondeau |
| 2002/0088063 A1 | 7/2002 | Ohashi et al. |
| 2002/0131941 A1 | 9/2002 | Habeck et al. |
| 2002/0176836 A9 | 11/2002 | Belli et al. |
| 2002/0176875 A9 | 11/2002 | Douin et al. |
| 2003/0000023 A9 | 1/2003 | Rondeau |
| 2003/0019052 A1 | 1/2003 | Pratt |
| 2003/0019053 A9 | 1/2003 | Rondeau |
| 2003/0055268 A1 | 3/2003 | Pasquier et al. |
| 2003/0074747 A1 | 4/2003 | Vuarier et al. |
| 2003/0124079 A1 | 7/2003 | Mougin et al. |
| 2003/0131424 A1 | 7/2003 | Audousset et al. |
| 2004/0019981 A1 | 2/2004 | Cottard et al. |
| 2004/0034945 A1 | 2/2004 | Javet et al. |
| 2004/0037796 A1 | 2/2004 | Cottard et al. |
| 2004/0049860 A1 | 3/2004 | Cottard et al. |
| 2004/0141943 A1 | 7/2004 | Mougin et al. |
| 2004/0148711 A1 | 8/2004 | Rondeau |
| 2004/0205901 A1 | 10/2004 | Cottard et al. |
| 2004/0258641 A1 | 12/2004 | Plos et al. |
| 2005/0005368 A1 | 1/2005 | Plos et al. |
| 2005/0005369 A1 | 1/2005 | Plos et al. |
| 2005/0008593 A1 | 1/2005 | Plos et al. |
| 2005/0028301 A1 | 2/2005 | Pastore |
| 2005/0144741 A1 | 7/2005 | Lang et al. |

FOREIGN PATENT DOCUMENTS

| | | |
|---|---|---|
| CA | 1255603 | 6/1989 |
| CH | 487 231 | 3/1970 |
| DE | 33 13 332 | 10/1984 |
| DE | 196 46 804 A1 | 5/1997 |
| DE | 199 23 438 A1 | 11/2000 |
| DE | 199 26 377 A1 | 12/2000 |
| DE | 100 29 441 A1 | 1/2002 |
| DE | 101 41 683 A1 | 6/2003 |
| DE | 101 48 844 A1 | 10/2003 |
| EP | 0 087 060 B1 | 8/1983 |
| EP | 0 095 238 A2 | 11/1983 |
| EP | 0 080 976 B1 | 9/1986 |
| EP | 0 173 109 | 10/1989 |
| EP | 0 370 470 B1 | 5/1990 |
| EP | 0 412 704 B1 | 2/1991 |
| EP | 0 412 707 B1 | 2/1991 |
| EP | 0 445 342 B1 | 9/1991 |
| EP | 0 486 135 B1 | 5/1992 |
| EP | 0 122 324 B2 | 2/1993 |
| EP | 0 337 354 B1 | 2/1994 |
| EP | 0 582 152 B1 | 2/1994 |
| EP | 0 395 282 | 3/1995 |
| EP | 0 503 853 | 5/1996 |
| EP | 0 714 954 A2 | 6/1996 |
| EP | 0 733 355 A2 | 9/1996 |
| EP | 0 815 828 B1 | 6/1999 |
| EP | 0 970 684 A1 | 1/2000 |
| EP | 1 023 891 B1 | 8/2000 |
| EP | 1 099 437 | 5/2001 |
| EP | 1 132 076 A1 | 9/2001 |
| EP | 1 133 977 A2 | 9/2001 |
| EP | 1 191 041 A2 | 3/2002 |
| FR | 1492597 | 9/1966 |
| FR | 1583363 | 10/1969 |
| FR | 2077143 | 10/1971 |
| FR | 2080759 | 11/1971 |
| FR | 2103210 | 7/1972 |
| FR | 2162025 | 7/1973 |
| FR | 2190406 | 2/1974 |
| FR | 2252840 | 6/1975 |
| FR | 2270846 | 12/1975 |
| FR | 2280361 | 2/1976 |
| FR | 2316271 | 1/1977 |
| FR | 2320330 | 3/1977 |
| FR | 2336434 | 7/1977 |
| FR | 2368508 | 5/1978 |
| FR | 2383660 | 10/1978 |
| FR | 2393573 | 1/1979 |
| FR | 2411219 | 7/1979 |
| FR | 2416723 | 9/1979 |
| FR | 2470596 | 6/1981 |
| FR | 2505348 | 11/1982 |
| FR | 2519863 | 7/1983 |
| FR | 2542997 | 9/1984 |

| | | |
|---|---|---|
| FR | 2586913 | 3/1987 |
| FR | 2589476 | 5/1987 |
| FR | 2598611 | 11/1987 |
| FR | 2692572 | 6/1992 |
| FR | 2741261 | 5/1997 |
| FR | 2 773 470 | 7/1999 |
| FR | 2 797 877 | 3/2001 |
| FR | 2800612 | 5/2001 |
| FR | 2811993 | 1/2002 |
| FR | 2820032 | 8/2002 |
| FR | 2830189 | 4/2003 |
| GB | 746864 | 3/1956 |
| GB | 759385 | 10/1956 |
| GB | 1214394 | 1/1970 |
| GB | 1546809 | 5/1979 |
| GB | 1554331 | 10/1979 |
| JP | 48-17362 | 5/1973 |
| JP | 54-86521 | 7/1979 |
| JP | 2-200612 | 8/1990 |
| JP | 6-128128 | 5/1994 |
| JP | 6-183935 | 7/1994 |
| JP | 6-227954 | 8/1994 |
| JP | 8-183716 | 7/1996 |
| JP | 8-208448 | 8/1996 |
| JP | 8-259426 | 10/1996 |
| JP | 9-183714 | 7/1997 |
| JP | 10-23629 | 9/1998 |
| JP | 11-021214 | 1/1999 |
| JP | 11-60453 | 3/1999 |
| JP | 11-343218 | 12/1999 |
| JP | 2000-01417 | 1/2000 |
| JP | 2000-86472 | 3/2000 |
| JP | 2000-505841 | 5/2000 |
| JP | 2001-172120 | 6/2001 |
| JP | 2001-220330 | 8/2001 |
| JP | 2001-226217 | 8/2001 |
| JP | 2001-261534 | 9/2001 |
| JP | 2001-261536 | 9/2001 |
| JP | 2001-294519 | 10/2001 |
| JP | 2001-302473 | 10/2001 |
| JP | 2001-516701 | 10/2001 |
| JP | 2001-516705 | 10/2001 |
| JP | 2001-516706 | 10/2001 |
| JP | 2001-516707 | 10/2001 |
| JP | 2002-12523 | 1/2002 |
| JP | 2002-12530 | 1/2002 |
| JP | 2002-47151 | 2/2002 |
| JP | 2002-226338 | 8/2002 |
| JP | 2002-249419 | 9/2002 |
| JP | 2002-326911 | 11/2002 |
| JP | 2003-55177 | 2/2003 |
| JP | 2004-059468 | 2/2004 |
| JP | 2004-307494 | 11/2004 |
| JP | 2004-307495 | 11/2004 |
| WO | WO 93/11103 | 6/1993 |
| WO | WO 93/23009 | 11/1993 |
| WO | WO 93/23446 | 11/1993 |
| WO | WO 94/02022 | 2/1994 |
| WO | WO 95/00578 | 1/1995 |
| WO | WO 95/01772 | 1/1995 |
| WO | WO 95/15144 | 6/1995 |
| WO | WO 97/18795 | 5/1997 |
| WO | WO 99/12846 | 3/1999 |
| WO | WO 99/13822 | 3/1999 |
| WO | WO 99/13823 | 3/1999 |
| WO | WO 99/13824 | 3/1999 |
| WO | WO 99/13828 | 3/1999 |
| WO | WO 99/13841 | 3/1999 |
| WO | WO 99/13844 | 3/1999 |
| WO | WO 99/13845 | 3/1999 |
| WO | WO 99/13846 | 3/1999 |
| WO | WO 99/13847 | 3/1999 |
| WO | WO 99/13849 | 3/1999 |
| WO | WO 99/20235 | 4/1999 |
| WO | WO 00/68282 | 11/2000 |
| WO | WO 00/71085 A2 | 11/2000 |
| WO | WO 01/43714 A1 | 6/2001 |
| WO | WO 01/62759 A1 | 8/2001 |
| WO | WO 01/78669 | 10/2001 |
| WO | WO 02/32386 A2 | 4/2002 |
| WO | WO 02/38115 A1 | 5/2002 |
| WO | WO 02/39964 A1 | 5/2002 |
| WO | WO 02/45673 A2 | 6/2002 |
| WO | WO 02/58646 A1 | 8/2002 |
| WO | WO 02/58647 A1 | 8/2002 |
| WO | WO 02/74270 | 9/2002 |
| WO | WO 03/22232 A2 | 3/2003 |
| WO | WO 03/28685 A1 | 4/2003 |
| WO | WO 03/029359 | 4/2003 |

OTHER PUBLICATIONS

Co-pending U.S. Appl. No. 10/742,995, filed Dec. 23, 2003.
Co-pending U.S. Appl. No. 10/814,334, filed Apr. 1, 2004.
Co-pending U.S. Appl. No. 10/814,333, filed Apr. 1, 2004.
Co-pending U.S. Appl. No. 10/814,430, filed Apr. 1, 2004.
Co-pending U.S. Appl. No. 10/814,305, filed Apr. 1, 2004.
Co-pending U.S. Appl. No. 10/814,300, filed Apr. 1, 2004.
Co-pending U.S. Appl. No. 10/814,335, filed Apr. 1, 2004.
Co-pending U.S. Appl. No. 10/814,428, filed Apr. 1, 2004.
Co-pending U.S. Appl. No. 10/490,869, filed Apr. 1, 2004.
Co-pending U.S. Appl. No. 10/814,236, filed Apr. 1, 2004.
Co-pending U.S. Appl. No. 10/814,338, filed Apr. 1, 2004.
Co-pending U.S. Appl. No. 10/814,585, filed Apr. 1, 2004.
Co-pending U.S. Appl. No. 10/814,336, filed Apr. 1, 2004.
English language Derwent Abstract for DE 33 13 332, published Oct. 18, 1984.
English Language Derwent Abstract of DE 100 29 441.
English Language Derwent Abstract of DE 101 41 683.
English Language Derwent Abstract of DE 101 48 844.
English Language Derwent Abstract of DE 199 23 438.
English Language Derwent Abstract of DE 199 26 377.
English Language Derwent Abstract of EP 0 080 976 B1.
English Language Derwent Abstract of EP 0 087 060 B1.
English Language Derwent Abstract of EP 1 023 891 B1.
English Language Derwent Abstract of EP 1 099 437.
English Language Derwent Abstract of FR 2,589,476 (EP 0 225 261) from EPO website.
English Language Derwent Abstract of FR 2 773,470.
English language abstract from esp@cenet for FR 2 797 877.
English Language Derwent Abstract of FR 2,800,612.
English Language Derwent Abstract of JP 2-200612.
English Language Derwent Abstract of JP 6-183935.
English Language Derwent Abstract of JP 6-227954.
English Language Derwent Abstract of JP 8-183716.
English Language Derwent Abstract of JP 8-208448.
English Language Derwent Abstract of JP 9-183714.
English Language Derwent Abstract of JP 10-23629.
English Language Derwent Abstract of JP 11-060453.
English Language Derwent Abstract of JP 11-21214.
English Language Derwent Abstract of JP 2000-1417.
English Language Derwent Abstract of JP 2000-086472.
English Language Derwent Abstract of JP 2001-172120.
English Language Derwent Abstract of JP 2001-220330.
English Language Derwent Abstract of JP 2001-261534.
English Language Derwent Abstract of JP 2001-294519.
English Language Derwent Abstract of JP 2001-302473.
English Language Derwent Abstract of JP 2001-516701.
English Language Derwent Abstract of JP 2001-516705.
English Language Derwent Abstract of JP 2001-516706.
English Language Derwent Abstract of JP 2001-516707.
English Language Derwent Abstract of JP 2002-226338.
English Language Abstract of JP 2002-249419 from Japio database.
English Language Derwent Abstract of JP 2002-326911.
English Language Derwent Abstract of JP 2004-59468.

French Search Report for French Patent Application No. FR 02/16669, priority document for U.S. Appl. No. 10/742,995, Aug. 6, 2003.
French Search Report for French Patent Application No. FR 03/04021, priority document for U.S. Appl. No. 10/814,337, (present case) Dec. 8, 2003.
French Search Report for French Patent Application No. FR 03/04022, priority document for co-pending U.S. Appl. No. 10/814,336, Nov. 20, 2003.
French Search Report for French Patent Application No. FR 03/04024, priority document for co-pending Appl. No. 10/814,585, Dec. 8, 2003.
French Search Report for French Patent Application No. FR 03/04026, priority document for co-pending U.S. Appl. No. 10/814,335, Nov. 21, 2003.
French Search Report for French Patent Application No. FR 03/04027, priority document for co-pending U.S. Appl. No. 10/814,428, Nov. 28, 2003.
French Search Report for French Patent Application No. FR 03/04028, priority document for co-pending U.S. Appl. No. 10/814,236, Nov. 25, 2003.
French Search Report for French Patent Application No. FR 03/04029, priority document for co-pending U.S. Appl. No. 10/814,430, Feb. 5, 2004.
French Search Report for French Patent Application No. FR 03/04030, priority document for co-pending U.S. Appl. No. 10/814,300, Nov. 27, 2003.
French Search Report for French Patent Application No. FR 03/04031, priority document for co-pending U.S. Appl. No. 10/814,333, Jan. 8, 2004.
French Search Report for French Patent Application No. FR 03/04033, priority document for co-pending U.S. Appl. No. 10/814,334, Nov. 28, 2003.
French Search Report for French Patent Application No. FR 03/04034, priority document for co-pending U.S. Appl. No. 10/814,338, Feb. 17, 2004.
French Search Report for French Patent Application No. FR 03/04035, priority document for co-pending U.S. Appl. No. 10/814,305, Feb. 5, 2004.
International Search Report for PCT Appl. No. PCT/FR 02/03252, (for co-pending U.S. Appl. No. 10/490,869), Jan. 20, 2003.
Office Action mailed Nov. 2, 2005 in co-pending U.S. Appl. No. 10/742,995.
Office Action mailed Nov. 2, 2005 in co-pending U.S. Appl. No. 10/814,338.
Office Action mailed Nov. 3, 2005 in co-pending U.S. Appl. No. 10/490,869.
Office Action mailed Nov. 17, 2005 in co-pending U.S. Appl. No. 10/814,336.
Office Action mailed Mar. 15, 2006, in co-pending U.S. Appl. 10/814,305.
Office Action mailed Mar. 23, 2006, in co-pending U.S. Appl. 10/814,300.
Office Action mailed Mar. 24, 2006 in co-pending U.S. Appl. 10/814,236.
Office Action mailed Mar. 27, 2006 in co-pending U.S. Appl. 10/814,334.
Office Action mailed May 18, 2006 in co-pending U.S. Appl. 10/814,333.
Office Action mailed May 25, 2006 in co-pending U.S. Appl. No. 10/814,335.
Office Action mailed May 26, 2006 in co-pending U.S. Appl. 10/490,869.
Office Action mailed Jun. 8, 2006 in co-pending U.S. Appl. 10/814,430.
Jacobi, Otto and Jacobi, Gertrud, "Investigation into the reciprocal action of cosmetics and the biosphere of the stratum corneuum of the skin," *Cosmetics and Toiletries*, 91:25-32 (Jan. 1976).
Science Des Traitements Capillaires [Hair Treatment Sciences] by Charles Zviak, 1988, published by Masson, pp. 215 and 278.
M. Schlossmann, "The Chemistry and Manufacture of Cosmetics Formulating," 2(3):522-526 (2000).
D.F. Williams et al., "Chemistry and Technology of the Cosmetics and Toiletries Industry," ed. 2, pp. 77-78 (1996).
Yuuki Kagoubutsu Jilen (Dictionary of Organic Compounds), Kodansha Ltd., Aug. 10, 2002, p. 908.
G. Fonnum, J. Bakke and Fk. Hansen—Colloid Polym. Sci 271, 380-389 (1993).
Zviak, C., The Science of Hair Care, pp. 215 and 278 (1986).

* cited by examiner

US 7,150,764 B2

COMPOSITION FOR DYEING A HUMAN KERATIN MATERIAL, COMPRISING AT LEAST ONE FLUORESCENT DYE AND AT LEAST ONE INSOLUBLE CONDITIONING AGENT, PROCESS THEREOF, USE THEREOF, AND DEVICES THEREOF

This application claims benefit of U.S. Provisional Application No. 60/468,063, filed May 6, 2003.

Disclosed herein is a composition comprising at least one fluorescent dye and at least one conditioning agent, and also to processes and a device for using these compositions. Further disclosed herein is the use of these compositions for dyeing with a lightening effect a human keratin material and, for example, keratin fibers such as artificially dyed or pigmented hair, and dark skin.

It is common for individuals with dark skin to wish to lighten their skin and for this purpose to use cosmetic or dermatological compositions comprising bleaching agents.

The substances most commonly used as bleaching agents are hydroquinone and derivatives thereof, kojic acid and derivatives thereof, azelaic acid, arbutin and derivatives thereof, alone or in combination with other active agents.

However, these agents may have some drawbacks. For example, they may need to be used for a long time and in large amounts in order to obtain a bleaching effect on the skin. It is possible that no immediate effect may be observed after applying compositions comprising these agents.

In addition, hydroquinone and derivatives thereof may be used in an amount that is effective to produce a visible bleaching effect. For example, hydroquinone is known for its cytotoxicity towards melanocyte.

Moreover, kojic acid and derivatives thereof may have the drawback of being expensive and consequently of not being useful in large amounts in products for commercial mass distribution.

There is thus still a need for cosmetic compositions that may allow the user to obtain a lighter, uniform, homogeneous skin tone with a natural appearance, while at the same time providing a satisfactory transparency after application to the skin.

In the field of haircare, there are mainly two types of hair dyeing.

The first is semi-permanent dyeing or direct dyeing, which uses dyes capable of giving the hair's natural color a more or less pronounced modification that can withstand shampooing several times. These dyes are known as direct dyes and may be used in two different ways. The colorations may be performed by applying the composition comprising the at least one direct dye directly to the keratin fibers, or by applying a mixture, prepared extemporaneously, of a composition comprising the at least one direct dye with a composition comprising at least one oxidizing bleaching agent, which may, for example, be aqueous hydrogen peroxide solution. Such a process is then termed "lightening direct dyeing".

The second type of hair dyeing is permanent dyeing or oxidation dyeing. This is performed with "oxidation" dye precursors, which are colorless or weakly colored compounds which, once mixed with oxidizing products, at the time of use, can give rise to colored compounds and dyes via a process of oxidative condensation. At least one direct dye may often be used with the oxidation bases and couplers in order to neutralize or attenuate the shades with too much of a red, orange or golden glint or, on the contrary, to accentuate these red, orange or golden glints.

Among the available direct dyes, nitrobenzene direct dyes may not be sufficiently strong, and indoamines, quinone dyes and natural dyes may have low affinity for keratin fibers and consequently lead to colorations that may not be sufficiently fast with respect to the various treatments to which the fibers may be subjected, and, for example, with respect to shampooing.

In addition, there is a need to obtain a lightening effect on human keratin fibers. This lightening may conventionally be obtained via a process of bleaching the melanins of the hair via an oxidizing system comprising hydrogen peroxide optionally combined with persalts. This bleaching system may have the drawback of degrading the keratin fibers and of impairing at least one of their cosmetic properties.

Therefore, there is still a need to solve a least one of the problems mentioned above and, for example, to propose a composition that has good dyeing affinity for a keratin material, for example, keratin fibers, has at least one good resistance property with respect to external agents, for example, shampooing, and that also may make it possible to obtain lightening without impairing the treated material, such as, keratin fibers.

It has thus been found, that the use of at least one fluorescent dye, for example, those in the orange range, in the presence of at least one conditioning agent, may allow at least one of these objectives to be achieved.

Disclosed herein is a composition, comprising, in a cosmetically acceptable medium,
  at least one fluorescent dye that is soluble in the medium and
  at least one conditioning agent that is insoluble in the medium, chosen from:
    synthetic oils;
    mineral oils;
    plant oils;
    animal oils;
    fluoro oils;
    perfluoro oils;
    natural and synthetic waxes;
    carboxylic acid esters; and
    compounds of formula $R_3CHOH-CH(NHCOR_1)-CH_2OR_2$, wherein
      $R_1$ is chosen from $C_{14}-C_{30}$ alkyl radicals, optionally substituted in at least one position chosen from the α position with at least one hydroxyl radical and the ω position with at least one hydroxyl radical esterified with at least one fatty acid chosen from $C_{16}-C_{30}$ fatty acids,
      $R_2$ is chosen from a hydrogen atom and (glycosyl)$_n$ and (galactosyl)$_m$ radicals wherein n is a number ranging from 1 to 4 and m is a number ranging from 1 to 8, and
      $R_3$ is chosen from $C_{15}-C_{26}$ hydrocarbon-based radicals optionally substituted with at least one radical chosen from alkyl radicals and $C_{15}-C_{26}$ α-hydroxyalkyl radicals optionally esterified with at least one $C_{16}-C_{30}$ α-hydroxy acid.

Further disclosed herein is process for dyeing human keratin fibers with a lightening effect, comprising,
  a) applying to the keratin fibers at least one composition as defined herein;
  b) leaving the composition on the keratin fibers for a time period that is sufficient to develop the desired coloration and lightening;
  c) optionally rinsing the keratin fibers;
  d) optionally washing the keratin fibers with shampoo and rinsing the keratin fibers; and e) drying or leaving the keratin fibers to dry.

Further disclosed herein is the use of the composition for dyeing a human keratin material with a lightening effect.

Even further disclosed herein is a multi-compartment device for dyeing and lightening keratin fibers, comprising at least one compartment comprising the at least one composition as defined herein, and at least one other compartment comprising at least one oxidizing composition comprising at least one oxidizing agent.

The compositions disclosed herein may, for example, allow better fixing of the at least one fluorescent dye onto the keratin material, which is reflected by an increased fluorescent effect and a lightening effect that is greater than that obtained with the at least one fluorescent dye used alone.

Better resistance of the result with respect to washing or shampooing may also be found.

However, other characteristics and advantages of the various embodiments disclosed herein will emerge more clearly on reading the description and the examples that follow.

Unless otherwise indicated, the limits of the ranges of values that are given in the description are included in these ranges.

As has been mentioned previously, the composition disclosed herein comprises at least one fluorescent dye and at least one insoluble conditioning agent.

As used herein, the term "fluorescent dye" means a dye which is a molecule that colors by itself, and thus absorbs light in the visible spectrum and possibly in the ultraviolet spectrum (wavelengths ranging from 360 to 760 nanometers), but which, in contrast with a standard dye, converts the absorbed energy into fluorescent light of a longer wavelength emitted in the visible region of the spectrum.

The at least one fluorescent dye disclosed herein is to be differentiated from an optical brightener. Optical brighteners, which are also known as brighteners, fluorescent brighteners, fluorescent brightening agents, fluorescent whitening agents, whiteners or fluorescent whiteners, are colorless transparent compounds. Optical brighteners do not dye because they do not absorb light in the visible region, but only in the ultraviolet region (wavelengths ranging from 200 to 400 nanometers), and convert the absorbed energy into fluorescent light of a longer wavelength emitted in the visible region of the spectrum. The color impression is then generated solely by purely fluorescent light that is predominantly blue (wavelengths ranging from 400 to 500 nanometers).

Finally, the at least one fluorescent dye used in the composition disclosed herein is soluble in the medium of the composition. It should be pointed out that the at least one fluorescent dye differs herein from a fluorescent pigment, which itself is insoluble in the medium of the composition.

For example, the at least one fluorescent dye used in the composition disclosed herein, which is optionally neutralized, is soluble in the medium of the composition to at least 0.001 g/l, further, for example, to at least 0.5 g/l, even further, for example, to at least 1 g/l and, according to yet another embodiment, to at least 5 g/l, at a temperature ranging from 15 to 25° C.

For example, the at least one fluorescent dye that may be used may, for example, be chosen from naphthalimides; cationic and non-cationic coumarins; xanthenodiquinolizines, such as sulphorhodamines; azaxanthenes; naphtholactams; azlactones; oxazines; thiazines; dioxazines; azo, azomethine and methine monocationic and polycationic fluorescent dyes. In one embodiment, the at least one fluorescent dye is chosen from naphthalimides; cationic and non-cationic coumarins; azaxanthenes; naphtholactams; azlactones; oxazines; thiazines; dioxazines; and azo, azomethine and methine monocationic and polycationic fluorescent dyes.

The at least one fluorescent dye may, for example, be chosen from dyes in the orange range.

For example, the at least one fluorescent dye has a reflectance maximum that is in the wavelength range from 500 to 650 nanometers and, for example, in the wavelength range from 550 to 620 nanometers.

The at least one fluorescent dye may be chosen from compounds that are known per se.

For example, the at least one fluorescent dye may be chosen from dyes having the following formulae:

Brilliant Yellow B6GL sold by the company Sandoz and having the following formula (F1):

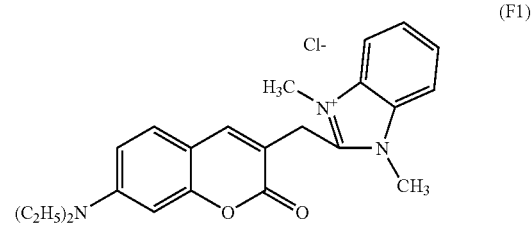

Basic Yellow 2, and Auramine O, sold by the companies Prolabo, Aldrich and Carlo Erba and having the following formula (F2):

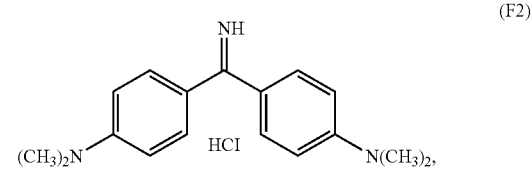

and 4,4'-(imidocarbonyl)bis(N,N-dimethylaniline) monohydrochloride—CAS number 2465-27-2.

Further examples of the at least one fluorescent dye include compounds having the following formula:

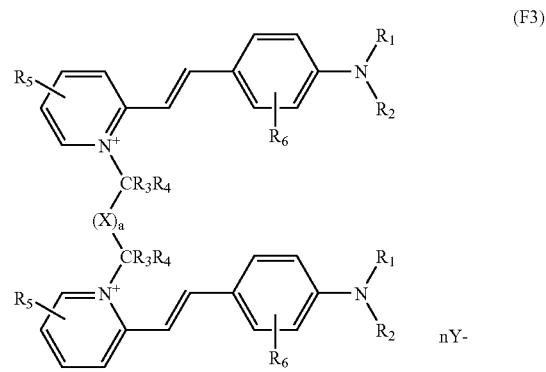

wherein:

$R_1$ and $R_2$, which may be identical or different, are each chosen from:

a hydrogen atom;

linear and branched alkyl radicals comprising from 1 to 10 carbon atoms and, for example, from 1 to 4 carbon atoms, optionally interrupted with at least one entity chosen from hetero atoms and groups comprising at least one hetero atom and/or optionally substituted with at least one entity chosen from hetero atoms, groups comprising at least one hetero atom, and halogen atoms;

aryl and arylalkyl radicals, wherein the aryl group comprises 6 carbon atoms and the alkyl radical comprises from 1 to 4 carbon atoms; wherein the aryl radical is optionally substituted with at least one alkyl radical chosen from linear and branched alkyl radicals comprising 1 to 4 carbon atoms optionally interrupted with at least one entity chosen from hetero atoms and groups comprising at least one hetero atom and/or optionally substituted with at least one hetero atom, groups comprising at least one hetero atom, and halogen atoms;

$R_1$ and $R_2$ may optionally form, together with the nitrogen to which they are attached, a heterocycle and may comprise at least one other hetero atom, wherein the heterocycle is optionally substituted with at least one alkyl radical chosen from linear and branched alkyl radicals, for example, comprising from 1 to 4 carbon atoms, wherein the at least one alkyl radical is optionally interrupted with at least one entity chosen from hetero atoms and groups comprising at least one hetero atom and/or optionally substituted with at least one entity chosen from hetero atoms, groups comprising at least one hetero atom, and halogen atoms; and $R_1$ or $R_2$ may optionally form, together with the nitrogen atom to which they are attached and one of the carbon atoms of the phenyl group bearing the nitrogen atom, a heterocycle.

$R_3$ and $R_4$, which may be identical or different, are each chosen from a hydrogen atom and alkyl radicals comprising from 1 to 4 carbon atoms;

$R_5$, which may be identical or different, is chosen from a hydrogen atom, halogen atoms, and linear and branched alkyl radicals comprising from 1 to 4 carbon atoms, optionally interrupted with at least one hetero atom;

$R_6$, which may be identical or different, is chosen from a hydrogen atom; halogen atoms; linear and branched alkyl radicals comprising from 1 to 4 carbon atoms, optionally substituted with at least one entity chosen from hetero atoms, groups comprising at least one hetero atom, and halogen atoms and/or optionally interrupted with at least one entity chosen from hetero atoms and groups bearing at least one hetero atom;

X is chosen from:

linear and branched alkyl radicals comprising from 1 to 14 carbon atoms and alkenyl radicals comprising from 2 to 14 carbon atoms, wherein the alkyl radicals and the alkenyl radicals are optionally interrupted with at least one entity chosen from hetero atoms and groups comprising at least one hetero atom and/or optionally substituted with at least one entity chosen from hetero atoms, groups comprising at least one hetero atom, and halogen atoms;

5- and 6-membered heterocyclic radicals optionally substituted with at least one alkyl radical chosen from linear and branched alkyl radicals comprising from 1 to 14 carbon atoms, optionally substituted with at least one entity chosen from hetero atoms; linear and branched aminoalkyl radicals comprising from 1 to 4 carbon atoms, optionally substituted with at least one hetero atom; and halogen atoms;

fused and non-fused aromatic and diaromatic radicals, optionally separated with at least one alkyl radical comprising from 1 to 4 carbon atoms, wherein the at least one aryl radical is optionally substituted with at least one entity chosen from halogen atoms and alkyl radicals comprising from 1 to 10 carbon atoms optionally substituted and/or interrupted with at least one entity chosen from hetero atoms and groups bearing at least one hetero atom;

a dicarbonyl radical; and wherein the group X bears at least one cationic charge;

a is equal to 0 or 1;

$Y^-$, which may be identical or different, is chosen from organic and mineral anions;

n is an integer equal to at least 2 and at most equal to the number of cationic charges present in the at least one fluorescent dye.

As used herein, the term "hetero atom" is an oxygen or nitrogen atom.

Examples of groups bearing such atoms include, inter alia, hydroxyl, alkoxy, carbonyl, amino, ammonium, amido (—N—CO—) and carboxyl (—O—CO— and —CO—O—) groups.

With regard to the alkenyl groups, they may comprise at least one unsaturated carbon-carbon bond (—C=C—) and, for example, only one carbon-carbon double bond.

In formula (F3), the radicals $R_1$ and $R_2$, which may be identical or different, may, for example, be chosen from:

a hydrogen atom;

alkyl radicals comprising from 1 to 10 carbon atoms, for example, from 1 to 6 carbon atoms and, for example, from 1 to 4 carbon atoms, optionally interrupted with an oxygen atom or optionally substituted with at least one entity chosen from hydroxyl, amino and ammonium radicals and chlorine and fluorine atoms;

benzyl and phenyl radicals optionally substituted with at least one radical chosen from alkyl and alkoxy radicals comprising from 1 to 4 carbon atoms and, for example, 1 or 2 carbon atoms;

with the nitrogen atom, a heterocyclic radical chosen from pyrrolo, pyrrolidino, imidazolino, imidazolo, imidazolium, pyrazolino, piperazino, morpholino, morpholo, pyrazolo and triazolo heterocyclic radicals, optionally substituted with at least one alkyl radical chosen from linear and branched alkyl radicals comprising from 1 to 4 carbon atoms optionally interrupted and/or substituted with at least one entity chosen from nitrogen and oxygen atoms and groups bearing at least one atom chosen from nitrogen and oxygen atoms.

With regard to the abovementioned amino or ammonium radicals, the radicals borne by the nitrogen atom may be identical or different and may, for example, be chosen from a hydrogen atom, $C_1$–$C_{10}$ and, for example, $C_1$–$C_4$ alkyl radicals and arylalkyl radical wherein, for example, the aryl radical comprises 6 carbon atoms and the alkyl radical comprises from 1 to 10 carbon atoms and, for example, from 1 to 4 carbon atoms.

In one embodiment, the radicals $R_1$ and $R_2$, which may be identical or different, are each chosen from a hydrogen atom; linear and branched $C_1$–$C_6$ alkyl radicals; $C_2$–$C_6$ alkyl radicals substituted with at least one hydroxyl radical; $C_2$–$C_6$ alkyl radicals bearing at least one group chosen from amino and ammonium groups; $C_2$–$C_6$ chloroalkyl radicals; $C_2$–$C_6$ alkyl radicals interrupted with at least one entity chosen from an oxygen atom and groups bearing at least one oxygen atom, for example, an ester; aromatic radicals, such as, phenyl, benzyl and 4-methylphenyl radicals; heterocyclic radicals such as pyrrolo, pyrrolidino, imidazolo, imidazolino, imidazolium, piperazino, morpholo, morpholino, pyrazolo and triazolo radicals, optionally substituted with at least one radical chosen from $C_1$–$C_6$ alkyl and aromatic radicals.

For example, the radicals $R_1$ and $R_2$, which may be identical or different, may each be chosen from a hydrogen atom, linear and branched $C_1$–$C_6$ alkyl radicals such as methyl, ethyl, n-butyl and n-propyl radicals; 2-hydroxyethyl; alkyltrimethylammonium and alkyltriethylammonium radicals, wherein the alkyl radical is chosen from linear $C_1$–$C_6$ alkyl radicals; (di)alkylmethylamino and (di)alkylethylamino radicals, wherein the alkyl radical is chosen from linear $C_1$–$C_6$ alkyl radicals; —$CH_2CH_2Cl$; —$(CH_2)_n$—$OCH_3$ and —$(CH_2)_nOCH_2CH_3$ wherein n is an integer ranging from 2 to 6; —$CH_2CH_2$—$OCOCH_3$; and —$CH_2CH_2COOCH_3$.

For example, the radicals $R_1$ and $R_2$, which may be identical or different, and which may, for example, be identical, may be chosen from methyl and ethyl radicals.

The radicals $R_1$ and $R_2$, which may be identical or different, may also be a heterocyclic radical chosen from pyrrolidino, 3-aminopyrrolidino, 3-(dimethyl)-aminopyrrolidino, 3-(trimethyl)aminopyrrolidino, 2,5-dimethylpyrrolo, 1H-imidazolo, 4-methylpiperazino, 4-benzylpiperazino, morpholo, 3,5-(tert-butyl)-1H-pyrazolo, 1H-pyrazolo and 1H-1,2,4-triazolo heterocyclic radicals.

The radicals $R_1$ and $R_2$, which may be identical or different, may also be chosen and be linked so as to form a heterocycle of formulae (I) and (II) below:

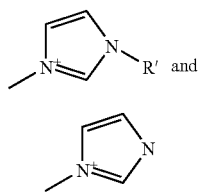

wherein R' is chosen from a hydrogen atom, $C_1$–$C_3$ alkyl radicals, —$CH_2CH_2OH$, and —$CH_2CH_2OCH_3$.

In another embodiment, $R_5$, which may be identical or different, is chosen from a hydrogen atom, fluorine and chlorine atoms, and linear and branched alkyl radicals comprising from 1 to 4 carbon atoms optionally interrupted with at least one atom chosen from oxygen and nitrogen atoms.

It is pointed out that the substituent $R_5$, if it is not a hydrogen atom, may be in at least one position chosen from positions 3 and 5 relative to the carbon of the ring bearing the nitrogen substituted with the radicals $R_1$ and $R_2$, and, for example, in position 3 relative to that carbon.

For example, the radicals $R_5$, which may be identical or different, may be chosen from a hydrogen atom; linear and branched $C_1$–$C_4$ alkyl radicals; —O—$R_{51}$ wherein $R_{51}$ is chosen from linear $C_1$–$C_4$ alkyl radicals; —$R_{52}$—O—$CH_3$ wherein $R_{52}$ is chosen from linear $C_2$–$C_3$ alkyl radicals; —$R_{53}$—$N(R_{54})_2$ wherein $R_{53}$ is chosen from linear $C_2$–$C_3$ alkyl radicals and $R_{54}$, which may be identical or different, is chosen from a hydrogen atom and a methyl radical.

For example, $R_5$, which may be identical or different, is chosen from a hydrogen atom and methyl and methoxy radicals. In one embodiment, $R_5$ may be a hydrogen atom.

In yet another embodiment, the radical $R_6$, which may be identical or different, is chosen from a hydrogen atom; linear and branched $C_1$–$C_4$ alkyl radicals; —X wherein X is chosen from chlorine, bromine and fluorine atoms; —$R_{61}$—O—$R_{62}$ wherein $R_{61}$ is chosen from linear $C_2$–$C_3$ alkyl radicals and $R_{62}$ is a methyl radical; —$R_{63}$—$N(R_{64})_2$ wherein $R_{63}$ is chosen from linear $C_2$–$C_3$ alkyl radicals and $R_{64}$, which may be identical or different, is chosen from a hydrogen atom and a methyl radical; —$N(R_{65})_2$ wherein $R_{65}$, which may be identical or different, is chosen from a hydrogen atom and linear $C_2$–$C_3$ alkyl radicals; —$NHCOR_{66}$ wherein $R_{66}$ is chosen from $C_1$–$C_2$ alkyl radicals, $C_1$–$C_2$ chloroalkyl radicals, and radicals —$R_{67}$—$NH_2$, —$R_{67}$—$NH(CH_3)$, —$R_{67}$—$N(CH_3)_2$, —$R_{67}$—$N^+(CH_3)_3$, and —$R_{67}N^+(CH_2CH_3)_3$ wherein $R_{67}$ is chosen from $C_1$–$C_2$ alkyl radicals.

It is pointed out that the substituent $R_6$, if it is not a hydrogen atom, may be in at least one position chosen from positions 2 and 4 relative to the nitrogen atom of the pyridinium ring, and, for example, in position 4 relative to that nitrogen atom.

For example, the radical $R_6$, which may be identical or different, is chosen from a hydrogen atom and methyl and ethyl radicals, and $R_6$ may, for example, be a hydrogen atom.

With regard to the radicals $R_3$ and $R_4$, these radicals, which may be identical or different, may, for example, be chosen from a hydrogen atom and alkyl radicals comprising from 1 to 4 carbon atoms and may, for example, be a methyl radical. In one embodiment, $R_3$ and $R_4$, may each be a hydrogen atom.

As mentioned above, X may be chosen from:
linear and branched alkyl radicals comprising from 1 to 14 carbon atoms and alkenyl radicals comprising from 2 to 14 carbon atoms, wherein the alkyl radicals and the alkenyl radicals are optionally interrupted with at least one entity chosen from hetero atoms and groups comprising at least one hetero atom and/or optionally substituted with at least one entity chosen from hetero atoms, groups comprising at least one hetero atom, and halogen atoms;
5- and 6-membered heterocyclic radicals optionally substituted with at least one alkyl radical chosen from linear and branched alkyl radicals comprising from 1 to 14 carbon atoms, optionally substituted with at least one entity chosen from hetero atoms; linear and branched aminoalkyl radicals comprising from 1 to 4 carbon atoms, optionally substituted with at least one hetero atom; and halogen atoms;
fused and non-fused aromatic and diaromatic radicals, optionally separated with at least one alkyl radical comprising from 1 to 4 carbon atoms, wherein the at least one aryl radical is optionally substituted with at least one entity chosen from halogen atoms and alkyl radicals comprising from 1 to 10 carbon atoms optionally substituted and/or interrupted with at least one entity chosen from hetero atoms and groups bearing at least one hetero atom; and
a dicarbonyl radical;
In addition, the group X may bear at least one cationic charge.

Thus, X may be chosen from linear and branched alkyl radicals comprising from 1 to 14 carbon atoms and alkenyl radicals comprising from 2 to 14 carbon atoms, wherein the alkyl and alkenyl radicals may be substituted with at least one entity chosen from oxygen and nitrogen atoms, groups bearing at least one hetero atom, and fluorine and chlorine atoms and/or optionally interrupted with at least one entity chosen from oxygen and nitrogen atoms and groups bearing at least one hetero atom.

Examples of groups of this type include hydroxyl, alkoxy (for example, having from 1 to 4 carbon atoms), amino, ammonium, amido, carbonyl and carboxyl groups (—COO— and —O—CO—), for example, with an alkyloxy radical.

It should be noted that the nitrogen atom, if it is present, may be in a quaternized or non-quaternized form. In this case, the other radical or the other two radicals borne by the quaternized or non-quaternized nitrogen atom is(are) identical or different and may be chosen from a hydrogen atom and $C_1$–$C_4$ alkyl radicals, for example, a methyl radical.

According to another embodiment, the group X is chosen from 5- and 6-membered heterocyclic imidazolo, pyrazolo, triazino and pyridino radicals, optionally substituted with at least one entity chosen from linear and branched alkyl radicals comprising from 1 to 14 carbon atoms, for example, from 1 to 10 carbon atoms and further, for example, from 1 to 4 carbon atoms; linear and branched aminoalkyl radicals comprising from 1 to 10 carbon atoms and, for example, from 1 to 4 carbon atoms, optionally substituted with at least one group comprising at least one hetero atom (for example, a hydroxyl radical), and halogen atoms. It should be noted that the amino group may, for example, be linked to the heterocycle.

In another embodiment, the group X is chosen from aromatic radicals (for example, comprising 6 carbon atoms) and fused and non-fused diaromatic radicals (for example, comprising from 10 to 12 carbon atoms), possibly separated with at least one alkyl radical comprising from 1 to 4 carbon atoms, wherein the at least one aryl radical is optionally substituted with at least one entity chosen from halogen atoms and alkyl radicals comprising from 1 to 10 carbon atoms and, for example, from 1 to 4 carbon atoms and/or optionally interrupted with at least one entity chosen from oxygen and nitrogen atoms and groups comprising at least one hetero atom, for example, carbonyl, carboxyl, amido, amino and ammonium radicals.

It should be noted that the aromatic radical, for example, a phenyl radical, may be linked to the groups $CR_3R_4$ via bonds in positions 1,2; 1,3 or 1,4 and, for example, in positions 1,3 and 1,4. If the phenyl radical linked via bonds in positions 1,4 and bears one or two substituents, this or these substituent(s) may, for example, be located in position 1,4 relative to one of the groups $CR_3R_4$. If the phenyl radical linked via bonds in positions 1,3 and bears one or two substituents, this or these substituents may, for example, be located in position 1 and/or 3 relative to one of the groups $CR_3R_4$.

In the case where the radical is diaromatic, it may, for example, be non-fused and comprise two phenyl radicals possibly separated with a single bond (i.e. a carbon of each of the two rings) or with an alkyl radical, for example, $CH_2$ or $C(CH_3)_2$ alkyl radical. For example, the aromatic radicals do not bear a substituent. It should be noted that the diaromatic radical may be linked to the groups $CR_3R_4$ via bonds in positions 4,4'.

Examples of group X include linear and branched alkyl radicals comprising from 1 to 13 carbon atoms, such as methylene, ethylene, propylene, isopropylene, n-butylene, pentylene and hexylene; 2-hydroxypropylene and 2-hydroxy-n-butylene; $C_1$–$C_{13}$ alkylene radicals substituted or interrupted with at least one entity chosen from nitrogen and oxygen atoms and groups bearing at least one hetero atom, for example, hydroxyl, amino, ammonium, carbonyl and carboxyl groups, such as —$CH_2CH_2OCH_2CH_2$—, 1,6-dideoxy-d-mannitol, —$CH_2N^+(CH_3)_2CH_2$—, —$CH_2CH_2N^+(CH_3)_2$-$(CH_2)_6N^+(CH_3)_2$-$CH_2CH_2$-, —CO—CO—, 3,3-dimethylpentylene, 2-acetoxyethylene, butylene-1,2,3,4-tetraol; —CH=CH—; aromatic and diaromatic radicals substituted with at least one entity chosen from alkyl radicals, groups bearing at least one hetero atom, and halogen atoms, such as 1,4-phenylene, 1,3-phenylene, 1,2-phenylene, 2,6-fluorobenzene, 4,4'-biphenylene, 1,3-(5-methylbenzene), 1,2-bis(2-methoxy)benzene, bis(4-phenyl)methane, methyl 3,4-benzoate and 1,4-bis(amidomethyl)phenyl; heterocyclic radicals such as pyridine, and derivatives thereof such as 2,6-bispyridine, imidazole, imidazolium and triazine.

In another embodiment, X is chosen from linear and branched $C_1$–$C_{13}$ alkyl radicals; —$CH_2CH(OH)CH_2$—; —$CH_2CH(Cl)CH_2$—; —$CH_2CH_2$—$OCOCH_2$—; —$CH_2CH_2COOCH_2$—; —Ra—O—Rb— wherein Ra is chosen from linear $C_2$–$C_6$ alkyl radicals and Rb is chosen from linear $C_1$–$C_2$ alkyl radicals; —Rc—N(Rd)—Re— wherein Rc is chosen from $C_2$–$C_9$ alkyl radicals, Rd is chosen from a hydrogen atom and $C_1$–$C_2$ alkyl radicals and Re is chosen from $C_1$–$C_6$ alkyl radicals; —Rf—$N^+(Rg)_2$—Rh— wherein Rf is chosen from linear $C_2$–$C_9$ alkyl radicals, Rg, which may be identical, is chosen from $C_1$–$C_2$ alkyl radicals and Rh is chosen from linear $C_1$–$C_6$ alkyl radicals; and —CO—CO—.

X may also be chosen from imidazole radicals, optionally substituted with at least one alkyl radical comprising from 1 to 14 carbon atoms, for example, from 1 to 10 carbon atoms and, for example, from 1 to 4 carbon atoms, for example, the divalent radicals having the following formula;

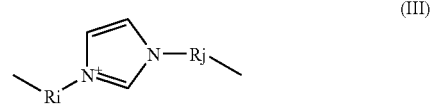

(III)

wherein Ri and Rj, which may be identical or different, are each chosen from linear $C_1$–$C_6$ alkyl radicals.

X may be chosen from the divalent triazine-based radicals below:

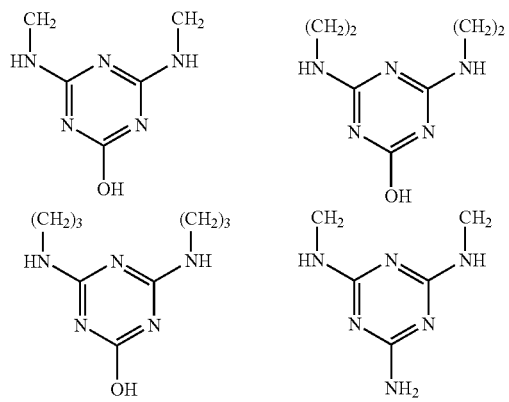

-continued

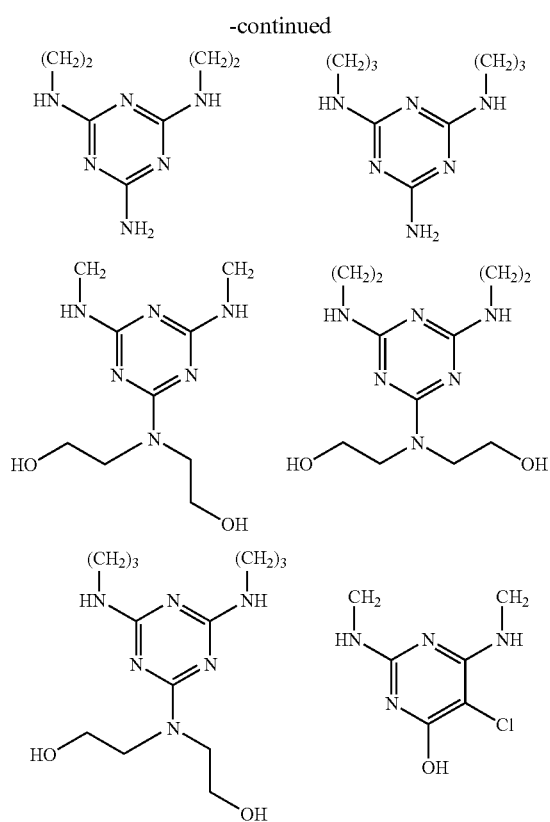

In yet another embodiment, X may be chosen from the divalent aromatic radicals below:

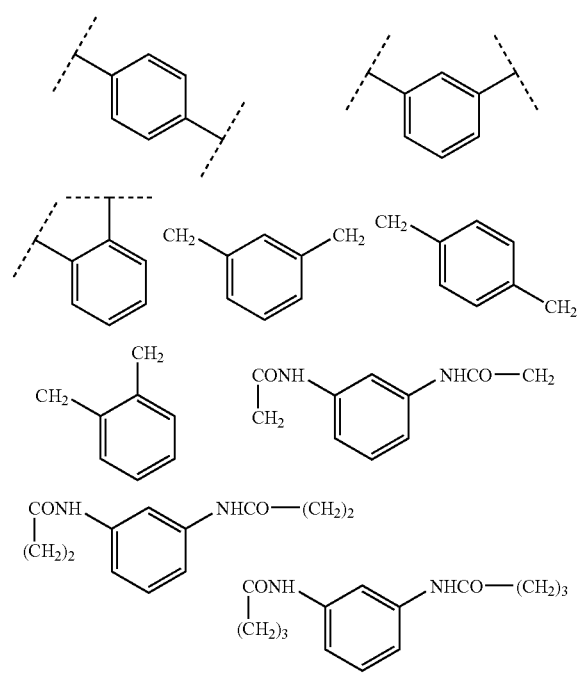

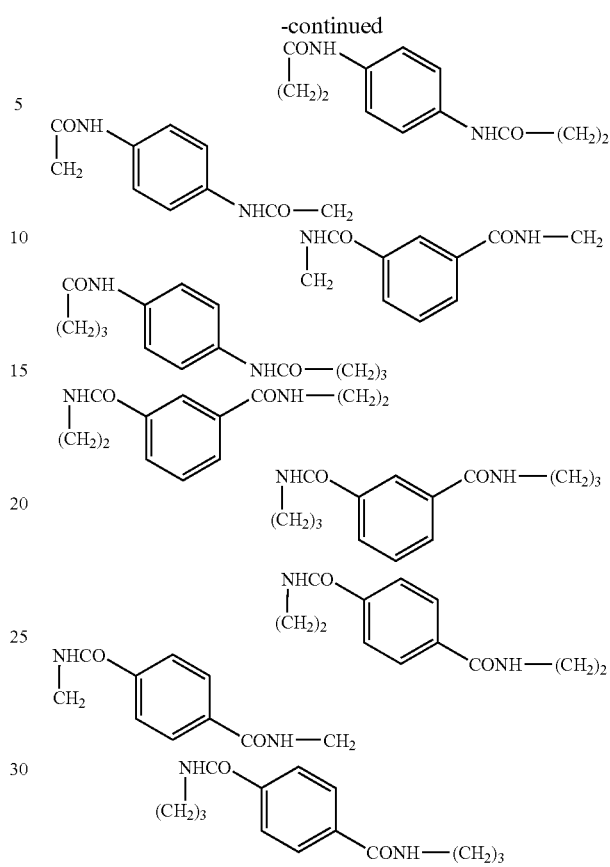

In formula (F3) of the at least one fluorescent dye, $Y^-$ is chosen from organic and mineral anions. If there are several anions $Y^-$, these anions may be identical or different.

Nonlimiting examples of anions of mineral origin include anions derived from halogen atoms, such as chlorides, iodides, sulphates and bisulphates, nitrates, phosphates, hydrogen phosphates, dihydrogen phosphates, carbonates and bicarbonates.

Nonlimiting examples of anions of organic origin include anions derived from the salts of saturated and unsaturated, aromatic and non-aromatic monocarboxylic and polycarboxylic, sulphonic and sulphuric acids, optionally substituted with at least one entity chosen from hydroxyl and amino radicals, and halogen atoms. Further non-limiting examples include acetates, hydroxyacetates, aminoacetates, (tri)chloroacetates, benzoxyacetates, propionates and derivatives thereof bearing at least one chlorine atom, fumarates, oxalates, acrylates, malonates, succinates, lactates, tartrates, glycolates, citrates, benzoates and derivatives thereof bearing at least one radical chosen from methyl and amino radicals, alkyl sulphates, tosylates, benzenesulphonates, and toluenesulphonates.

For example, the anion(s) Y, which may be identical or different, may be chosen from chloride, sulphate, methosulphate and ethosulphate.

Finally, the integer n is at least equal to 2 and at most equal to the number of cationic charges present in the at least one fluorescent dye.

For example, the at least one fluorescent dye is a symmetrical compound.

These compounds may be synthesized by reacting, in a first step, α-picoline with a reagent comprising two leaving groups that may be chosen from halogen atoms, for example, bromine, chlorine, tolylsulphonyl groups and methanesulphonyl groups.

This first step may take place in the presence of a solvent, although this is not obligatory, for example, dimethylformamide.

The number of moles of α-picoline is generally in the region of 2 per mole of reagent comprising the leaving groups.

In addition, the reaction is usually performed at the reflux temperature of the reagent and/or of the solvent if a solvent is present.

The product derived from this first step is then placed in contact with a corresponding aldehyde having the following formula:

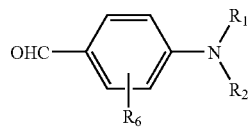

wherein $R_1$, $R_2$ and $R_6$ have the same meanings as indicated above.

In this case also, the reaction may be performed in the presence of a suitable solvent, which is, for example, at reflux.

It should be noted that the radicals $R_1$ and $R_2$ of the aldehyde may have the meaning indicated in formula (F3) detailed previously.

It is also possible to use an aldehyde for which the radicals are hydrogen atoms and to perform, in accordance with standard methods, the substitution of these hydrogen atoms with suitable radicals as described in formula (F3) once the second step is complete.

Reference may be made, for example, to syntheses as described in U.S. Pat. No. 4,256,458.

It is similarly possible to use compounds having the following structure:

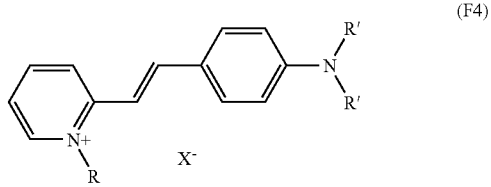

(F4)

wherein R is chosen from methyl and ethyl radicals; R' is a methyl radical and $X^-$ is chosen from anions such as chloride, iodide, sulphate, methosulphate, acetate and perchlorate.

An example of a compound of this type is the Photosensitizing Dye NK-557 sold by the company Ubichem, wherein R is an ethyl radical, R' is a methyl radical and $X^-$ is an iodide.

For example, the at least one fluorescent dye is chosen from naphthalimides; cationic and non-cationic coumarins; xanthenodiquinolizines (such as sulphorhodamines); azaxanthenes; naphtholactams; azlactones; oxazines; thiazines; dioxazines; and azo, azomethine and methine polycationic fluorescent dyes. In one embodiment, the at least one fluorescent dye is chosen from naphthalimides; cationic and non-cationic coumarins; azaxanthenes; naphtholactams; azlactones; oxazines; thiazines; dioxazines; and azo, azomethine and methine polycationic fluorescent dyes.

Examples of such compounds include the compounds of formulae (F1) to (F3).

In one embodiment, the composition doesn't comprise a compound of formula (F4).

The at least one fluorescent dye may be present in the composition disclosed herein in an amount ranging from 0.01% to 20% by weight, for example, from 0.05% to 10% by weight, and, even further, for example, from 0.1% to 5% by weight, relative to the total weight of the composition.

As mentioned previously, the composition disclosed herein comprises, besides the at least one fluorescent dye, at least one conditioning agent that is insoluble in the medium of the composition.

As used herein, the term "conditioning agent" means any agent whose function is to improve at least one of the cosmetic properties of a keratin material such as the hair, for example, softness, disentangling, feel, smoothness and static electricity.

In addition, the expression "insoluble in the medium of the composition"means any compound which, in all or a part of the concentration ranging from 0.01% to 20% by weight, at room temperature, in the medium of the composition, does not form a macroscopically isotropic transparent solution under these conditions.

It should be noted that, in one embodiment, the at least one conditioning agent may, for example, be in a dispersed form in the medium of the composition in the form of particles generally having a number-average size ranging from 2 nanometers to 100 microns and, for example, ranging from 30 nanometers to 20 microns (measured with a granulometer).

Thus, the at least one conditioning agent may, for example, be chosen from synthetic oils; mineral oils; plant oils; fluoro oils and perfluoro oils; natural and synthetic waxes; carboxylic acid esters; and compounds of the formula $R_3CHOH-CH(NHCOR_1)-CH_2OR_2$, wherein $R_1$ is chosen from $C_{14}-C_{30}$ alkyl radicals, optionally substituted in at least one position chosen from the α position with at least one hydroxyl radical and the ω position with at least one hydroxyl radical esterified with at least one fatty acid chosen from $C_{16}-C_{30}$ fatty acids, $R_2$ is chosen from a hydrogen atom and (glycosyl)n and (galactosyl)m radicals wherein n is a number ranging from 1 to 4 and m is a number ranging from 1 to 8, and $R_3$ is chosen from $C_{15}-C_{26}$ hydrocarbon-based radicals optionally substituted with at least one radical chosen from alkyl radicals and $C_{15}-C_{26}$ α-hydroxyalkyl radicals optionally esterified with at least one $C_{16}-C_{30}$ α-hydroxy acid.

For example, the at least one conditioning agent may be chosen from synthetic oils; plant oils; fluoro oils and perfluoro oils; natural and synthetic waxes; carboxylic acid esters; and compounds of the formula $R_3CHOH-CH(NHCOR_1)-CH_2OR_2$, wherein $R_1$, $R_2$, and $R_3$ have the above-mentioned definitions.

In one embodiment, the synthetic oils are chosen from polyolefins, such as poly-α-olefins and, further, for example, chosen from:

hydrogenated and non-hydrogenated polybutene poly-α-olefins and, for example, hydrogenated and non-hydrogenated polyisobutenes;

Isobutylene oligomers with a weight-average molecular mass of less than 1000 g/mol and mixtures thereof with polyisobutylenes with a weight-average molecular mass of greater than 1000 g/mol and, for example, ranging from 1000 to 15 000 g/mol may, for example, be used.

Examples of poly-α-olefins that can be used include polyisobutenes sold under the name PERMETHYL 99 A, 101 A, 102 A, 104 A (n=16) and 106 A (n=38) by the company Presperse Inc., and the products sold under the name ARLAMOL HD (n=3) by the company ICI (n denoting the degree of polymerization), and hydrogenated and non-hydrogenated polydecene poly-α-olefins.

Such products are sold, for example, under the names ETHYLFLO by the company Ethyl Corp. and ARLAMOL Pao by the company ICI.

The animal and plant oils may, for example, be chosen from sunflower oil, corn oil, maize oil, soybean oil, avocado oil, jojoba oil, marrow oil, grapeseed oil, sesame oil, hazelnut oil, fish oils, glyceryl tricaprocaprylate, and plant and animal oils of formula $R_9COOR_{10}$, wherein $R_9$ is chosen from higher fatty acid residues comprising from 7 to 29 carbon atoms and $R_{10}$ is chosen from linear and branched hydrocarbon-based chains comprising from 3 to 30 carbon atoms, for example, alkyl and alkenyl hydrocarbon-based chains, such as purcellin oil and liquid jojoba wax.

It is also possible to use natural and synthetic essential oils, for example, chosen from eucalyptus oil, lavendin oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil.

The waxes may be chosen from natural (animal and plant) and synthetic substances that are solid at room temperature (20°–25° C.). They may be insoluble in water and soluble in oils.

For the definition of waxes, mention may be made, for example, of P. D. Dorgan, Drug and Cosmetic Industry, December 1983, pp. 30–33, the disclosure relating to this definition are incorporated herein by reference.

The waxes may, for example, be chosen from at least one of carnauba wax, candelilla wax, alfalfa wax, paraffin wax, ozokerite, plant waxes such as olive tree wax, rice wax, hydrogenated jojoba wax and the absolute waxes of flowers such as the essential wax of blackcurrant flower sold by the company Bertin (France), animal waxes such as beeswaxes, and modified beeswaxes (cerabellina); other waxes and waxy starting materials which can be used include, for example, marine waxes such as the product sold by the company Sophim under the reference M82, and polyethylene waxes and polyolefin waxes in general.

The compounds corresponding to formula $R_3CHOH$—CH($NHCOR_1$)—$CH_2OR_2$ may, for example, be chosen from at least one of N-linoleyldihydrosphingosine, N-oleyldihydrosphingosine, N-palmitoyldihydrosphingosine, N-stearoyldihydrosphingosine, N-behenoyldihydrosphingosine.

The fluoro oils may, for example, be chosen from perfluoropolyethers described in, for example, in Patent Application No. EP-A-486 135 and the fluorohydrocarbon compounds described, for example, in Patent Publication No. WO 93/11103. The teaching of these two patent applications is incorporated herein in its entirety by reference.

As used herein, the term "fluorohydrocarbon compounds" means compounds whose chemical structure comprises a carbon skeleton in which certain hydrogen atoms have been replaced with fluorine atoms.

The fluoro oils can also chosen from fluorocarbons such as fluoroamines, for example perfluorotributylamine, fluorohydrocarbons, for example, perfluorodecahydronaphthalene, fluoro esters and fluoro ethers.

The perfluoropolyethers are sold, for example, under the trade names FOMBLIN by the company Montefluos and KRYTOX by the company Du Pont.

Examples of fluorohydrocarbon compounds include fluorine-comprising fatty acid esters such as the products sold under the name NOFABLE FO by the company Nippon Oil.

The fatty alcohols may be chosen from linear and branched $C_8$–$C_{22}$ fatty alcohols; they may be optionally oxyalkylenated with 1 to 15 mol of alkylene oxide or polyglycerolated with 1 to 6 mol of glycerol. The alkylene oxide may, for example, be chosen from at least one of ethylene oxide and propylene oxide.

The carboxylic acid esters may, for example, be chosen from monocarboxylic, dicarboxylic, tricarboxylic and tetracarboxylic esters.

The monocarboxylic acid esters may, for example, be chosen from linear and branched, saturated and unsaturated $C_1$–$C_{26}$ aliphatic acid monoesters of linear and branched, saturated and unsaturated, $C_1$–$C_{26}$ aliphatic alcohols, wherein the total carbon number of the esters is greater than or equal to 10.

Examples of monoesters include dihydroabietyl behenate; octyldodecyl behenate; isocetyl behenate; cetyl lactate; $C_{12}$–$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl and 2-octyldodecyl myristate, hexyl stearate, butyl stearate, isobutyl stearate; dioctyl malate, hexyl laurate, and 2-hexyldecyl laurate.

$C_4$–$C_{22}$ di- and tricarboxylic acid esters of $C_1$–$C_{22}$ alcohols and mono-, di- and tricarboxylic acid esters of $C_2$–$C_{26}$ di-, tri-, tetra- and pentahydroxy alcohols can also be used.

Examples of such esters include diethyl sebacate; diisopropyl sebacate; diisopropyl adipate; di-n-propyl adipate; dioctyl adipate; diisostearyl adipate; dioctyl maleate; glyceryl undecylenate; octyldodecylstearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate dicaprate; tridecyl erucate; triisopropyl citrate; triisostearyl citrate; glyceryl trilactate; glyceryl trioctanoate; trioctyldodecyl citrate; and trioleyl citrate.

The esters may be chosen from ethyl and isopropyl palmitates, 2-ethylhexyl palmitate, 2-octyldecyl palmitate, alkyl myristates such as isopropyl, butyl, cetyl and 2-octyldodecyl myristate, hexyl stearate, butyl stearate, isobutyl stearate; dioctyl malate, hexyl laurate, 2-hexyldecyl laurate, isononyl isononanoate, and cetyl octanoate.

The at least one conditioning agent may be present in an amount ranging from 0.01% to 20% by weight, relative to the total weight of the composition and, for example, from 0.1% to 10% by weight, relative to the total weight of the composition.

The cosmetically acceptable medium may be chosen from water and mixtures of water and at least one common organic solvent.

The at least one common organic solvent may be chosen from alcohols such as ethyl alcohol, isopropyl alcohol, benzyl alcohol and phenylethyl alcohol, and glycols and glycol ethers, such as ethylene glycol monomethyl ether, monoethyl ether and monobutyl ether, propylene glycol and ethers thereof, such as propylene glycol monomethyl ether, butylene glycol, dipropylene glycol and diethylene glycol alkyl ethers, such as diethylene glycol monoethyl ether and monobutyl ether, and polyols, such as glycerol. Polyethylene glycols and polypropylene glycols, and mixtures of all these compounds, may also be used as the at least one common organic solvent.

The at least one common organic solvent described, if present, is in an amount ranging from 1% to 40% by weight, and, for example, from 5% to 30% by weight, relative to the total weight of the composition.

The pH of the composition disclosed herein may range from 3 to 12 and, for example, from 5 to 11.

It may be adjusted to the desired value by means of acidifying or basifying agents.

Examples of acidifying agents include mineral and organic acids, for example, hydrochloric acid, orthophosphoric acid, sulphuric acid, carboxylic acids, such as, acetic acid, tartaric acid, citric acid and lactic acid, and sulphonic acids.

Examples of basifying agents include aqueous ammonia, alkaline carbonates, alkanolamines such as monoethanolamine, diethanolamine and triethanolamine and derivatives thereof, sodium hydroxide, potassium hydroxide and the compounds of formula (A) below:

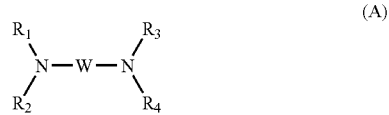

(A)

wherein W is chosen from propylene residues optionally substituted with at least one entity chosen from a hydroxyl group and $C_1$–$C_6$ alkyl radicals; $R_1$, $R_2$, $R_3$ and $R_4$, which may be identical or different, are each chosen from a hydrogen atom and $C_1$–$C_6$ alkyl and $C_1$–$C_6$ hydroxyalkyl radicals.

In one embodiment, the composition disclosed herein may comprise, in addition to the at least one fluorescent dye, at least one additional non-fluorescent direct dye chosen from nonionic, cationic and anionic direct dyes, which may be chosen, for example, from nitrobenzene dyes.

For example, the at least one additional non-fluorescent direct dye may be chosen from red and orange nitrobenzene direct dyes chosen from:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine and
1-amino-2-nitro-4-hydroxy-5-methylbenzene.

The composition disclosed herein may also comprise, in addition to or in replacement for these nitrobenzene dyes, at least one additional non-fluorescent direct dye chosen from yellow, green-yellow, blue and violet nitrobenzene dyes, nitrobenzene dyes, azo dyes, anthraquinone dyes, naphthoquinone dyes, benzoquinone dyes, phenothiazine dyes, indigoid dyes, xanthene dyes, phenanthridine dyes and phthalocyanin dyes, and triarylmethane-based dyes.

The at least one additional non-fluorescent direct dye may, for example, be chosen from basic dyes. Examples of these basic dyes include those known in the Color Index, 3rd edition, under the names "Basic Brown 16", "Basic Brown 17", "Basic Yellow 57", "Basic Red 76", "Basic Violet 10", "Basic Blue 26" and "Basic Blue 99", acidic direct dyes, such as, the dyes known in the Color Index, 3rd edition, under the names "Acid Orange 7", "Acid Orange 24", "Acid Yellow 36", "Acid Red 33", "Acid Red 184", "Acid Black 2", "Acid Violet 43"and "Acid Blue 62", and cationic direct dyes such as those described in Patent Publication Nos. WO 95/01772, WO 95/15144 and Patent Application No. EP 714 954, the content of which relates to the cationic direct dyes forms is incorporated herein by reference.

The yellow and green-yellow nitrobenzene direct dyes may, for example, be chosen from the following compounds:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene and
4-(β-hydroxyethyl)amino-3-nitrobenzamide.

The blue and violet nitrobenzene direct dyes may, for example, be chosen from the following compounds:
1-(β-hydroxyethyl)amino-4-N,N-bis(β-hydroxyethyl) amino-2-nitrobenzene,
1-(γ-hydroxypropyl)amino-4,N,N-bis(β-hydroxyethyl) amino-2-nitrobenzene,
1-(β-hydroxyethyl)amino-4-(N-methyl-N-β-hydroxyethyl) amino-2-nitrobenzene,
1-(β-hydroxyethyl)amino-4-(N-ethyl-N-β-hydroxyethyl) amino-2-nitrobenzene, 1-(β,γ-dihydroxypropyl)amino-4-(N-ethyl-N-β-hydroxyethyl)amino-2-nitrobenzene,
2-nitroparaphenylenediamines having the following formula:

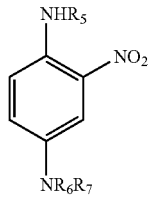

wherein:
R$_6$ is chosen from C$_1$–C$_4$ alkyl radicals and β-hydroxyethyl, β-hydroxypropyl and γ-hydroxypropyl radicals;
R$_5$ and R$_7$, which may be identical or different, are each chosen from β-hydroxyethyl, β-hydroxypropyl, γ-hydroxypropyl and β,γ-dihydroxypropyl radical, wherein at least one of the radicals R$_6$, R$_7$ or R$_5$ is a γ-hydroxypropyl radical and R$_6$ and R$_7$ are not simultaneously a β-hydroxyethyl radical when R$_5$ is a γ-hydroxypropyl radical, such as those described in Patent No. FR 2 692 572.

The at least one additional non-fluorescent direct dye, if present, is in an amount ranging from 0.0005% to 12% by weight, relative to the total weight of the composition, and even, further, for example, from 0.005% to 6% by weight, relative to the total weight of the composition.

When it is intended for oxidation dyeing, the composition comprises, in addition to the at least one fluorescent dye, at least one oxidation base chosen from the oxidation bases conventionally used for oxidation dyeing, for example, para-phenylenediamines, bis(phenyl)alkylenediamines, para-aminophenols, ortho-aminophenols and heterocyclic bases, and the addition salts thereof with an acid or with an alkaline agent.

The para-phenylenediamines may, for example, be chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy)pyrrolidine, and the addition salts thereof with an acid or with an alkaline agent.

The para-phenylenediamines may, for example, be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid or with an alkaline agent.

The bis(phenyl)alkylenediamines may, for example, be chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid or with an alkaline agent.

The para-aminophenols may, for example, be chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

The ortho-aminophenols may, for example, be chosen from 2-aminophenol, 2-amino-5-methylphenol, 2-amino-6-methylphenol and 5-acetamido-2-aminophenol, and the addition salts thereof with an acid or with an alkaline agent.

The heterocyclic bases may, for example, be chosen from pyridine derivatives, pyrimidine derivatives and pyrazole derivatives, and the addition salts thereof with an acid or with an alkaline agent.

The at least one oxidation base, if present, is in an amount ranging from 0.0005% to 12% by weight relative to the total weight of the composition and, for example, ranging from 0.005% to 6% by weight, relative to the total weight of the composition.

When it is intended for oxidation dyeing, the composition disclosed herein may also comprise, in addition to the at least one fluorescent dye and the at least one oxidation base, at least one coupler to modify or to enrich with glints the shades obtained using the at least one fluorescent dye and the at least one oxidation base.

The at least one coupler that may be used in the composition disclosed herein may, for example, be chosen from couplers conventionally used in oxidation dyeing, for example, meta-phenylenediamines, meta-aminophenols, meta-diphenols and heterocyclic couplers, and the addition salts thereof with an acid or with an alkaline agent.

The at least one coupler may, for example, be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, and the addition salts thereof with an acid or with an alkaline agent.

The at least one coupler, if present, is in an amount ranging from 0.0001% to 10% by weight and, for example, from 0.005% to 5% by weight, relative to the total weight of the composition.

In general, the addition salts with an acid that may be used in the composition disclosed herein for the at least one oxidation base and at least one coupler may, for example, be chosen from hydrochlorides, hydrobromides, sulphates, citrates, succinates, tartrates, tosylates, benzenesulphonates, lactates, and acetates.

The addition salts with an alkaline agent that may be used in the composition disclosed herein for the at least one oxidation base and at least one coupler may, for example, be chosen from the addition salts with alkali metals and alkaline-earth metals, with ammonia and with organic amines, including alkanolamines and the compounds of formula (A) described above.

The composition disclosed herein may also comprise at least one conventional adjuvant, for example, chosen from anionic, cationic, nonionic, amphoteric and zwitterionic surfactants, anionic, cationic, nonionic, amphoteric and zwitterionic polymers other than the polymers disclosed herein, mineral thickeners, antioxidants, penetrating agents, sequestering agents, fragrances, buffers, dispersants, conditioners, such as cations, film-forming agents, preserving agents, stabilizers and opacifiers.

The thickeners may, for example, be chosen from thickening systems based on associative polymers that are well known to those skilled in the art. For example, the thickeners can be chosen from nonionic, anionic, cationic and amphoteric thickening systems.

The surfactants may be chosen from nonionic, anionic and amphoteric surfactants. The surfactants may be present in an amount ranging from 0.01% to 30% by weight, relative to the total weight of the composition.

Needless to say, a person skilled in the art will take care to select this or these optional additional compound(s) such that the advantageous properties intrinsically associated with the composition disclosed herein is not, or are not, substantially adversely affected by the envisaged addition(s).

The composition disclosed herein may be in various forms, such as in a form chosen from liquids, shampoos, creams, gels, and any other suitable forms.

In one embodiment, the composition disclosed herein is in the form of a lightening dye shampoo comprising, in a cosmetically acceptable aqueous medium, at least one fluorescent dye that is soluble in the medium and at least one conditioning agent that is insoluble in the medium.

For example, the lightening dye shampoo may comprise at least one surfactant chosen from anionic, cationic, amphoteric and nonionic surfactants. An example of the nonionic surfactants include alkylpolyglycosides.

In these shampoos, the at least one surfactant may be present in an amount ranging from 4% to 30% by weight, and, for example, from 8% to 20% by weight, relative to the total weight of the shampoo composition.

In the composition disclosed herein, when at least one oxidation base is used, optionally in the presence of at least one coupler, or when the at least one fluorescent dye is used in the context of a lightening direct dyeing, then the composition disclosed herein may also comprise at least one oxidizing agent.

The at least one oxidizing agent may be chosen, for example, from hydrogen peroxide, urea peroxide, alkali metal bromates, persalts such as perborates and persulphates, and enzymes such as peroxidases and two-electron and four-electron oxidoreductases. In one embodiment, the at least one oxidation base is chosen from hydrogen peroxide and enzymes.

Further disclosed herein is the use of a composition as described herein for coloring a human keratin material with a lightening effect.

As used herein, the term "human keratin materials" means skin, hair, nails, eyelashes and eyebrows, and, for example, dark skin and artificially colored or pigmented hair.

As used herein, the term "dark skin" means a skin whose lightness $L^*$ measured in the CIEL $L^*a^*b^*$ system is less than or equal to 45 and, for example, less than or equal to 40, given that $L^*=0$ is equivalent to black and $L^*=100$ is equivalent to white. The skin types corresponding to this lightness are African skin, African-American skin, Latin-American skin, Indian skin and North African skin.

As used herein, the expression "artificially dyed or pigmented hair" means hair whose tone height is less than or equal to 6 (dark blond) and, for example, less than or equal to 4 (chestnut-brown).

The lightening of the hair is evaluated by the "tone height", which describes the degree or level of lightening. The notion of "tone" is based on the classification of the natural shades, one tone separating each shade from the shade immediately following or preceding it. This definition and the classification of the natural shades are well known to hairstyling professionals and are published in the book "Sciences des Traitements Capillaires [Hair Treatment Sciences]" by Charles Zviak, 1988, published by Masson, pp. 215 and 278, the disclosure relating to this definition and classification are incorporated herein by reference.

The tone heights range from 1 (black) to 10 (light blond), one unit corresponding to one tone; the higher the figure, the lighter the shade.

Further disclosed herein is a process for dyeing human keratin fibers with a lightening effect, comprising:
(a) applying at least one composition, comprising in a cosmetically acceptable medium,
at least one fluorescent dye that is soluble in the medium and
at least one conditioning agent that is insoluble in the medium, chosen from:
synthetic oils;
mineral oils;
plant oils;
animal oils;
fluoro oils;
perfluoro oils;
natural and synthetic waxes;
carboxylic acid esters; and
compounds of formula $R_3CHOH-CH(NHCOR_1)-CH_2OR_2$, wherein
$R_1$ is chosen from $C_{14}-C_{30}$ alkyl radicals, optionally substituted in at least one position chosen from the α position with at least one hydroxyl radical and the ω position with at least one hydroxyl radical esterified with at least one fatty acid chosen from $C_{16}-C_{30}$ fatty acids,
$R_2$ is chosen from a hydrogen atom and (glycosyl)n and (galactosyl)m radicals wherein n is a number ranging from 1 to 4 and m is a number ranging from 1 to 8, and
$R_3$ is chosen from $C_{15}-C_{26}$ hydrocarbon-based radicals optionally substituted with at least one radical chosen from alkyl radicals and $C_{15}-C_{26}$ α-hydroxyalkyl radicals optionally esterified with at least one $C_{16}-C_{30}$ α-hydroxy acid;

b) leaving the at least one composition on the keratin fibers to act for a time period sufficient to develop the desired coloration and lightening;
c) optionally rinsing the keratin fibers;
d) optionally washing the keratin fibers with shampoo and optionally rinsing the keratin fibers; and
e) drying or leaving to dry the keratin fibers.

Further disclosed herein is a process for coloring dark skin with a lightening effect, comprising applying the at least one composition that has just been described to the skin and drying the skin or leaving the skin to dry. For example, the at least one composition does not comprise the at least one oxidation base or the at least one coupler and is not used in the presence of at least one oxidizing agent.

Everything that has been described previously regarding the various constituent components of the composition disclosed herein remains valid, and reference may be made thereto.

For example, the processes disclosed herein are suitable for treating human keratin fibers, and, for example, artificially colored or pigmented hair, or dark skin.

In one embodiment, the fibers that may be treated with the process disclosed herein having a tone height of less than or equal to 6 (dark blond) and, for example, less than or equal to 4 (chestnut-brown).

Furthermore, dark skin capable of being treated in accordance with the process disclosed herein has a lightness L*, measured in the CIEL L*a*b* system, of less than or equal to 45 and, for example, less than or equal to 40.

In one embodiment, the process of dyeing fibers with a lightening effect is performed with a composition that does not comprise the at least one oxidation base or the at least one coupler and in the absence of the at least one oxidizing agent.

In yet another embodiment, the process of dyeing fibers with a lightening effect is performed with a composition that does not comprise the at least one oxidation base or the at least one coupler, but in the presence of at least one oxidizing agent.

According to one aspect of the dyeing processes disclosed herein, at least one composition as defined herein is applied to the fibers, such as hair, the at least one composition is left on the fibers for a time period that is sufficient to develop the desired coloration and lightening, the fibers are rinsed, optionally washed with shampoo and rinsed again, and dried.

According to another aspect of the dyeing processes disclosed herein, at least one composition as defined herein is applied to the fibers, such as hair, without final rinsing.

According to yet another aspect of the dyeing process disclosed herein, the dyeing process comprises separately storing at least one composition as defined herein which optionally includes at least one oxidation base and/or at least one coupler; and at least one oxidizing composition comprising, in a cosmetically acceptable medium, at least one oxidizing agent; and mixing the at least one composition and the at least one oxidizing composition at the time of use, applying the mixture to the keratin fibers, such as hair, leaving the mixture on the keratin fibers to act for a time period that is sufficient to develop the desired coloration, rinsing the fibers, and optionally washing with shampoo, optionally rinsing again and optionally drying the keratin fibers.

The time period required to develop the coloration and to obtain the lightening effect on the fibers, for example, the hair, ranges from 5 to 60 minutes and, for example, from 5 to 40 minutes.

The temperature required to develop the coloration and to obtain the lightening effect may, for example, range from room temperature (15 to 25° C.) to 80° C. and, for example, from 15 to 40° C.

Further disclosed herein is a multi-compartment device for dyeing keratin fibers, such as hair, with a lightening effect, comprising at least one compartment comprising at least one composition defined herein, and at least one other compartment comprising at least one oxidizing composition comprising at least one oxidizing agent. This device may be equipped with a means for applying the desired mixture to the fibers, such as the devices described in Patent No. FR 2 586 913.

It should be noted that the composition disclosed herein, if it is used to treat keratin fibers, for example, chestnut-brown hair, may make it possible to achieve the following results:

If the reflectance of the hair is measured when it is irradiated with visible light in the wavelength range from 400 to 700 nanometers, and if the curves of reflectance as a function of the wavelength are compared for hair treated with the composition disclosed herein and untreated hair, it was found that the reflectance curve corresponding to the treated hair, in a wavelength range from 500 to 700 nanometers, was higher than that corresponding to the untreated hair.

This means that, in the wavelength range from 500 to 700 nanometers, and, for example, from 540 to 700 nanometers, there is at least one range in which the reflectance curve corresponding to the treated hair is higher than the reflectance curve corresponding to the untreated hair. The term "higher than" means a difference of at least 0.05% and, for example, of at least 0.1% of reflectance.

However, it is pointed out that there may be, within the wavelength range from 500 to 700 nanometers and, for example, from 540 to 700 nanometers, at least one range wherein the reflectance curve corresponding to the treated fibers is either superimposable on or lower than the reflectance curve corresponding to the untreated fibers.

For example, the wavelength at which the difference is maximal between the reflectance curve for the treated hair and that for the untreated hair is in the wavelength range from 500 to 650 nanometers and, for example, in the wavelength range from 550 to 620 nanometers.

In addition, for example, the composition disclosed herein is capable of lightening hair and skin in a shade which, measured in the CIEL L*a*b* system, has a variable b* of greater than or equal to 6, with a b*/absolute value of a* ratio of greater than 1.2 according to the selection test described below.

Selection Test

The composition was applied to chestnut-brown keratin fibers, such as hair, at a rate of 10 grams of composition per 1 gram of chestnut-brown fibers. The composition was spread on so as to cover all of the fibers. The composition was left to act for 20 minutes at room temperature (20 to 25° C.). The fibers were then rinsed with water and then washed with a shampoo based on lauryl ether sulphate. They were then dried. The spectrocolorimetric characteristics of the fibers were then measured in order to determine the L*a*b* coordinates.

In the CIEL L*a*b* system, a* and b* indicate two color axes: a* indicates the green/red color axis (+a* is red, −a* is green) and b* indicates the blue/yellow color axis (+b* is yellow and −b* is blue); values close to zero for a* and b* correspond to grey shades.

The example that follows is intended to illustrate the embodiments disclosed herein without, however, limiting its scope.

EXAMPLES

Fluorescent Compound

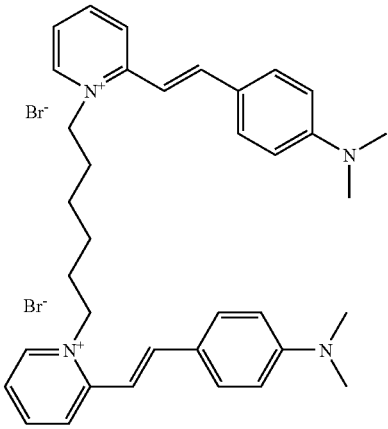

93 g of 2-picoline were reacted with 120 g of 1,6-dibromohexane in dimethylformamide at 110° C. for 5 hours.

The precipitated product was recovered and filtered off.

109 g of the product obtained above was dissolved in methanol and 82.82 g of p-dimethylaminobenzaldehyde were added in two portions, in the presence of pyrrolidine.

The mixture was then left for 30 minutes.

The product was recovered in precipitated form.

Analysis by mass spectroscopy: 266.

Elemental analysis: C, 62.43%; H, 6.40%; Br, 23.07%; N, 8.09%.

The formula was as follows: $C_{36}H_{44}N_4 \cdot 2Br$.

Compositions

The following compositions were prepared:

| Composition | 1 | 2 |
|---|---|---|
| Fluorescent compound | 0.6% | 0.6% |
| Isopropyl myristate | — | 0.25% |
| Arlamol HD (*) | 0.25% | — |
| Sodium lauryl ether sulphate (2.2 EO) | 10% | 10% |
| Distilled water | qs 100% | qs 100% |

Percentages expressed by weight of active material
(*) Arlamol HD: poly-α-olefin.

Each composition was applied to a lock of chestnut-brown natural hair of tone height 4 with a leave-in time of 20 minutes, a final rinsing operation and a drying operation under a hood for 30 minutes.

In each case, a lock of hair with a marked lightening effect was obtained.

What is claimed is:

1. A composition, comprising, in a cosmetically acceptable medium,
   at least one fluorescent dye that is soluble in the medium, wherein the at least one fluorescent dye is chose from compounds of the following formulae:

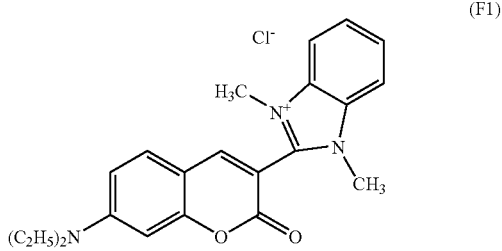

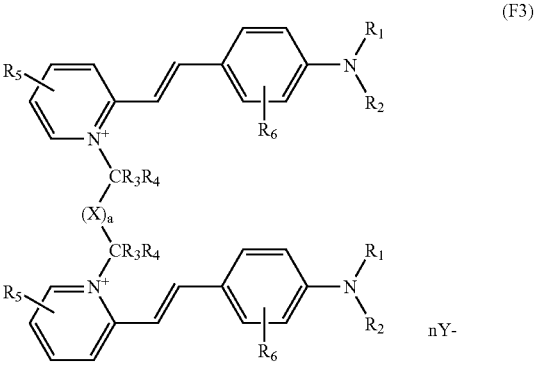

wherein:
  $R_1$ and $R_2$, which may be identical or different, are each chosen from:
    a hydrogen atom;
    linear and branched alkyl radicals comprising from 1 to 10 carbon atoms, wherein the alkyl radicals are optionally interrupted with at least one entity chosen from hetero atoms and groups comprising at least one hetero atom and/or optionally substituted with at least one entity chosen from hetero atoms, groups comprising at least one hetero atom, and halogen atoms;
    aryl and arylalkyl radicals, wherein the aryl group comprises 6 carbon atoms and the alkyl radical comprises from 1 to 4 carbon atoms; and wherein the aryl radical is optionally substituted with at least one alkyl radical chosen from linear and branched alkyl radicals comprising 1 to 4 carbon atoms optionally interrupted with at least one entity chosen from hetero atoms and groups comprising at least one hetero atom and/or optionally substituted with at least one entity chosen from hetero atoms, groups comprising at least one hetero atom, and halogen atoms;
  $R_1$ and $R_2$ may optionally form, together with the nitrogen to which they are attached, a heterocycle and may comprise at least one other hetero atom, wherein the heterocycle is optionally substituted with at least one alkyl radical chosen from linear and branched alkyl radicals, wherein the at least one alkyl radical is optionally interrupted with at least one entity chosen from hetero atoms and groups comprising at least one hetero atom and/or optionally substituted with at least one entity chosen from hetero atoms, groups comprising at least one hetero atom, and halogen atoms;

$R_1$ or $R_2$ may optionally form, together with the nitrogen atom to which they are attached and one of the carbon atoms of the phenyl group bearing the nitrogen atom, a heterocycle;

$R_3$ and $R_4$, which may be identical or different, are each chosen from a hydrogen atom and alkyl radicals comprising from 1 to 4 carbon atoms;

$R_5$, which may be identical or different, is chosen from a hydrogen atom, a halogen atom and linear and branched alkyl radicals comprising from 1 to 4 carbon atoms, optionally interrupted with at least one hetero atom;

$R_6$, which may be identical or different, is chosen from a hydrogen atom; a halogen atom; linear and branched alkyl radicals comprising from 1 to 4 carbon atoms, wherein the alkyl radicals are optionally substituted with at least one entity chosen from hetero atoms, groups bearing at least one hetero atom, and halogen atoms and/or optionally interrupted with at least one entity chosen from hetero atoms and groups bearing at least one hetero atom;

X is chosen from:
  linear and branched alkyl radicals comprising from 1 to 14 carbon atoms and alkenyl radicals comprising from 2 to 14 carbon atoms, wherein the alkyl and alkenyl radicals are optionally interrupted with at least one entity chosen from hetero atoms and groups comprising at least one hetero atom and/or optionally substituted with at least one entity chosen from hetero atoms, groups comprising at least one hetero atom, and halogen atoms;
  5- and 6-membered heterocyclic radicals optionally substituted with at least one alkyl radical chosen from linear and branched alkyl radicals comprising from 1 to 14 carbon atoms, optionally substituted with at least one entity chosen from hetero atoms; linear and branched aminoalkyl radicals comprising from 1 to 4 carbon atoms, optionally substituted with at least one hetero atom; and halogen atoms;
  fused and non-fused aromatic and diaromatic radicals, optionally separated with at least one alkyl radical comprising from 1 to 4 carbon atoms, the at least one aryl aromatic and diaromatic radicals radical is optionally substituted with at least one entity chosen from halogen atoms and alkyl radicals comprising from 1 to 10 carbon atoms optionally substituted and/or interrupted with at least one entity chosen from hetero atoms and groups bearing at least one hetero atom;
  a dicarbonyl radical; and
  wherein the group X possibly bears at least one cationic charge;

a is equal to 0 or 1;

$Y^-$, which may be identical or different, is chosen from organic and mineral anions; and n is an integer equal to at least 2 and at most equal to the number of cationic charges present in the at least one fluorescent dye; and

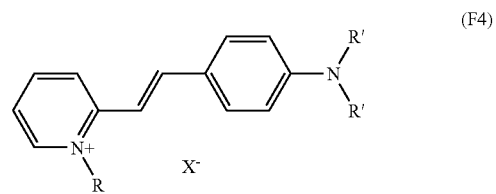

wherein R is chosen from methyl and ethyl radicals; R' is a methyl radical and $X^-$ is chosen from anions and at least one conditioning agent that is insoluble in the medium, chosen from:
  synthetic oils;
  mineral oils;
  plant oils;
  animal oils;
  fluoro oils;
  perfluoro oils;
  natural and synthetic waxes;
  carboxylic acid esters; and
  compounds of formula $R_3CHOH-CH(NH-COR_1)-CH_2OR_2$, wherein
    $R_1$ is chosen from $C_{14}-C_{30}$ alkyl radicals, optionally substituted in at least one position chosen from the α position with at least one hydroxyl radical and the ω position with at least one hydroxyl radical esterified with at least one fatty acid chosen from $C_{16}-C_{30}$ fatty acids,
    $R_2$ is chosen from a hydrogen atom and (glycosyl)$_n$ and (galactosyl)$_m$ radicals wherein n is a number ranging from 1 to 4 and m is a number ranging from 1 to 8, and
    $R_3$ is chosen from $C_{15}-C_{26}$ hydrocarbon-based radicals optionally substituted with at least one radical chosen from alkyl radicals and $C_{15}-C_{26}$ α-hydroxyalkyl radicals optionally esterified with at least one $C_{16}-C_{30}$ α-hydroxy acid.

2. The composition according to claim 1, wherein the at least one fluorescent dye has a reflectance maximum that is in the wavelength range from 500 to 650 nanometers.

3. The composition according to claim 2, wherein the at least one fluorescent dye has a reflectance maximum that is in the wavelength range from 550 to 620 nanometers.

4. The composition according to claim 1, wherein, in formula (F3), $R_1$ and $R_2$, which may be identical or different, are each chosen from linear and branched alkyl radicals comprising from 1 to 4 carbon atoms.

5. The composition according to claim 1, wherein, in formula (F3), the heterocycle formed from $R_1$ and $R_2$ and the nitrogen to which they are attached, is optionally substituted with at least one alkyl radical chosen from linear and branched alkyl radicals comprising from 1 to 4 carbon atoms.

6. The composition according to claim 1, wherein, in formula (F4), $X^-$ is chosen from chloride, iodide, sulphate, methosulphate, acetate and perchlorate anions.

7. The composition according to claim 1, wherein the at least one fluorescent dye is chosen from dyes in the orange range.

8. The composition according to claim 1, wherein the at least one fluorescent dye is present in an amount ranging from 0.01% to 20% by weight, relative to the total weight of the composition.

9. The composition according to claim 8, wherein the at least one fluorescent dye is present in an amount ranging from 0.05% to 10% by weight, relative to the total weight of the composition.

10. The composition according to claim 9, wherein the at least one fluorescent dye is present in an amount ranging from 0.1% to 5% by weight, relative to the total weight of the composition.

11. The composition according to claim 1, wherein the at least one fluorescent dye is soluble in the medium of the at least one composition to at least 0.001 g/l at a temperature ranging from 15 to 25° C.

12. The composition according to claim 11, wherein the at least one fluorescent dye is soluble in the medium of the at least one composition to at least 0.5 g/l at a temperature ranging from 15 to 25° C.

13. The composition according to claim 12, wherein the at least one fluorescent dye is soluble in the medium of the at least one composition to at least 1 g/l at a temperature ranging from 15 to 25° C.

14. The composition according to claim 13, wherein the at least one fluorescent dye is soluble in the medium of the at least one composition to at least 5 g/l at a temperature ranging from 15 to 25° C.

15. The composition according to claim 1, wherein the at least one insoluble conditioning agent is chosen from
synthetic oils chosen from polyolefins;
animal and plant oils chosen from sunflower oil, corn oil, maize oil, soybean oil, avocado oil, jojoba oil, marrow oil, grapeseed oil, sesame seed oil, hazelnut oil, fish oils, glyceryl tricaprocaprylate, plant and animal oils of formula $R_9COOR_{10}$ wherein $R_9$ is chosen from $C_7$–$C_{29}$ fatty acid residues and $R_{10}$ is chosen from linear and branched $C_3$–$C_{30}$ hydrocarbon-based chains; and natural and synthetic essential oils;
natural animal and plant waxes, and synthetic waxes;
N-linoleyldihydrosphingosine, N-oleyldihydrosphingosine, N-palmitoyldihydrosphingosine, N-stearoyldihydrosphingosine and N-behenoyldihydrosphingosine;
fluoro oils chosen from perfluoropolyethers, fluorohydrocarbon oils, fluorocarbons and fluorinated hydrocarbons;
fatty alcohols chosen from linear and branched $C_8$–$C_{22}$ fatty alcohols, optionally oxyalkylenated with 1 to 15 mol of alkylene oxide and polyglycerolated with 1 to 6 mol of glycerol; and
carboxylic acid esters chosen from linear and branched, saturated and unsaturated $C_1$–$C_{26}$ aliphatic monocarboxylic acid esters of saturated aliphatic alcohols, wherein the total carbon number of the esters is greater than or equal to 10; mono-, di-, tri-, tetra- and pentaesters of dicarboxylic and tricarboxylic acids and of $C_1$–$C_{22}$ alcohols and of $C_2$–$C_{26}$ di-, tri-, tetra- and pentahydroxy alcohols.

16. The composition according to claim 15, wherein the polyolefins are chosen from poly-α-olefins.

17. The composition according to claim 1, wherein the at least one insoluble conditioning agent is present in an amount ranging from 0.01% to 20% by weight, relative to the weight of the composition.

18. The composition according to claim 17, wherein the at least one insoluble conditioning agent is present in an amount ranging from 0.1% to 10% by weight, relative to total weight of the composition.

19. The composition according to claim 1, further comprising at least one surfactant chosen from nonionic, anionic and amphoteric surfactants.

20. The composition according to claim 19, wherein the at least one surfactant is present in an amount ranging from 0.01% to 30% by weight, relative to the total weight of the composition.

21. The composition according to claim 1, further comprising at least one non-fluorescent additional direct dye chosen from nonionic, cationic and anionic direct dyes.

22. The composition according to claim 1, wherein the at least one non-fluorescent additional direct dye is chosen from nitrobenzene dyes, azo dyes, anthraquinone dyes, naphthoquinone dyes, benzoquinone dyes, phenothiazine dyes, indigoid dyes, xanthene dyes, phenanthridine dyes, phthalocyanin dyes and triaryl-methane-based dyes.

23. The composition according to claim 22, wherein the at least one non-fluorescent additional direct dye is present in an amount ranging from 0.0005% to 12% by weight, relative to the total weight of the composition.

24. The composition according to claim 23, wherein the at least one non-fluorescent additional direct dye is present in an amount ranging from 0.005% to 6% by weight, relative to the total weight of the composition.

25. The composition according to claim 1, wherein the composition is in the form of a lightening dyeing shampoo.

26. The composition according to claim 1, further comprising at least one oxidation base chosen from para-phenylenediamines, bis(phenyl)alkylenediamines, para-aminophenols, ortho-aminophenols and heterocyclic bases, and the addition salts thereof with an acid or with an alkaline agent.

27. The composition according to claim 26, wherein the at least one oxidation base is present in an amount ranging from 0.0005% to 12% by weight, relative to the total weight of the composition.

28. The composition according to claim 27, wherein the at least one oxidation base is present in an amount ranging from 0.005% to 6% by weight, relative to the total weight of the composition.

29. The composition according to claim 1, further comprising at least one coupler chosen from meta-phenylenediamines, meta-aminophenols, meta-diphenols and heterocyclic couplers, and the addition salts thereof with an acid or with an alkaline agent.

30. The composition according to claim 29, wherein the at least one coupler is present in an amount ranging from 0.0001% to 10% by weight, relative to the total weight of the dye composition.

31. The composition according to claim 30, wherein the at least one coupler is present in an amount ranging from 0.005% to 5% by weight, relative to the total weight of the dye composition.

32. The composition according to claim 1, further comprising at least one oxidizing agent.

33. The composition according to claim 32, wherein the at least one oxidizing agent is chosen from hydrogen peroxide, urea peroxide, alkali metal bromates, persalts, enzymes, and two-electron and four-electron oxidoreductases.

34. The composition according to claim 33, wherein the persalts are chosen from perborates and persulphates.

35. The composition according to claim 33, wherein the enzymes are chosen from peroxidases.

36. The composition according to claim 33, wherein the at least one oxidizing agent is hydrogen peroxide.

37. A process for dyeing human keratin fibers with a lightening effect, comprising,
a) applying at least one composition, comprising in a cosmetically acceptable medium,
at least one fluorescent dye that is soluble in the medium, wherein the at least one fluorescent dye is chose from compounds of the following formulae:

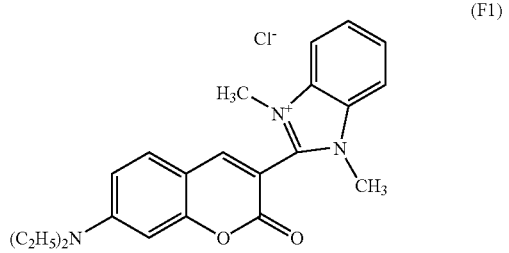

wherein;
$R_1$ and $R_2$ which may be identical or different, are each chosen from:
a hydrogen atom;
linear and branched alkyl radicals comprising from 1 to 10 carbon atoms, wherein the alkyl radicals are optionally interrupted with at least one entity chosen from hetero atoms and groups comprising at least one hetero atom and/or optionally substituted with at least one entity chosen from hetero atoms, groups comprising at least one hetero atom, and halogen atoms;
aryl and arylalkyl radicals, wherein the aryl group comprises 6 carbon atoms and the alkyl radical comprises from 1 to 4 carbon atoms; and wherein the aryl radical is optionally substituted with at least one alkyl radical chosen from linear and branched alkyl radicals comprising 1 to 4 carbon atoms optionally interrupted with at least one entity chosen from hetero atoms and groups comprising at least one hetero atom and/or optionally substituted with at least one entity chosen from hetero atoms, groups comprising at least one hetero atom, and halogen atoms;
$R_1$ and $R_2$ may optionally form, together with the nitrogen to which they are attached, a heterocycle and may comprise at least one other hetero atom, wherein the heterocycle is optionally substituted with at least one alkyl radical chosen from linear and branched alkyl radicals, wherein the at least one alkyl radical is optionally interrupted with at least one entity chosen from hetero atoms and groups comprising at least one hetero atom and/or optionally substituted with at least one entity chosen from hetero atoms, groups comprising at least one hetero atom, and halogen atoms;
$R_1$ or $R_2$ may optionally form, together with the nitrogen atom to which they are attached and one of the carbon atoms of the phenyl group bearing the nitrogen atom, a heterocycle;
$R_3$ and $R_4$, which may be identical or different, are each chosen from a hydrogen atom and alkyl radicals comprising from 1 to 4 carbon atoms;
$R_5$, which may be identical or different, is chosen from a hydrogen atom, a halogen atom and linear and branched alkyl radicals comprising from 1 to 4 carbon atoms, optionally interrupted with at least one hetero atom;
$R_6$, which may be identical or different, is chosen from a hydrogen atom; a halogen atom; linear and branched alkyl radicals comprising from 1 to 4 carbon atoms, wherein the alkyl radicals are optionally substituted with at least one entity chosen from hetero atoms, groups bearing at least one hetero atom, and halogen atoms and/or optionally interrupted with at least one entity chosen from hetero atoms and groups bearing at least one hetero atom;
X is chosen from;
linear and branched alkyl radicals comprising from 1 to 14 carbon atoms and alkenyl radicals comprising from 2 to 14 carbon atoms, wherein the alkyl and alkenyl radicals are optionally interrupted with at least one entity chosen from hetero atoms and groups comprising at least one hetero atom and/or optionally substituted with at least one entity chosen from hetero atoms, groups comprising at least one hetero atom, and halogen
5- and 6-membered heterocyclic radicals optionally substituted with at least one alkyl radical chosen from linear and branched alkyl radicals comprising from 1 to 14 carbon atoms, optionally substituted with at least one entity chosen from hetero atoms; linear and branched aminoalkyl radicals comprising from 1 to 4 carbon atoms, optionally substituted with at least one hetero atom; and halogen atoms;
fused and non-fused aromatic and diaromatic radicals, optionally separated with at least one alkyl radical comprising from 1 to 4 carbon atoms, the at least one aryl aromatic and diaromatic radicals radical is optionally substituted with at least one entity chosen from halogen atoms and alkyl radicals comprising from 1 to 10 carbon atoms optionally substituted and/or interrupted with at least one entity chosen from hetero atoms and groups bearing at least one hetero atom;
a dicarbonyl radical; and
wherein the group X possibly bears at least one cationic charge;
a is equal to 0 or 1;
$Y_-$, which may be identical or different, is chosen from organic and mineral anions; and
n is an integer equal to at least 2 and at most equal to the number of cationic charges present in the at least one fluorescent dye; and

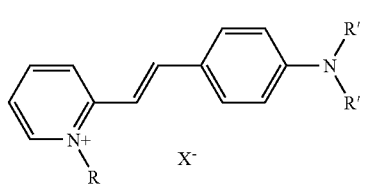

(F4)

wherein R is chosen from methyl and ethyl radicals; R' is a methyl radical and X⁻ is chosen from anions
and
at least one conditioning agent that is insoluble in the medium, chosen from:
synthetic oils;
mineral oils;
plant oils;
animal oils;
fluoro oils;
perfluoro oils;
natural and synthetic waxes;
carboxylic acid esters; and
compounds of formula $R_3CHOH-CH(NH-COR_1)-CH_2OR_2$, wherein
$R_1$ is chosen from $C_{14}-C_{30}$ alkyl radicals, optionally substituted in at least one position chosen from the α position with at least one hydroxyl radical and the ω position with at least one hydroxyl radical esterified with at least one fatty acid chosen from $C_{16}-C_{30}$ fatty acids,
$R_2$ is chosen from a hydrogen atom and $(glycosyl)_n$ and $(galactosyl)_m$ radicals wherein n is a number ranging from 1 to 4 and m is a number ranging from 1 to 8, and
$R_3$ is chosen from $C_{15}-C_{26}$ hydrocarbon-based radicals optionally substituted with at least one radical chosen from alkyl radicals and $C_{15}-C_{26}$ α-hydroxyalkyl radicals optionally esterified with at least one $C_{16}-C_{30}$ α-hydroxy acid;
b) leaving the at least one composition on the keratin fibers to act for a time period sufficient to develop the desired coloration and lightening;
c) optionally rinsing the keratin fibers;
d) optionally washing the keratin fibers with shampoo and optionally rinsing the keratin fibers; and
e) drying or leaving to dry the keratin fibers.
38. A process comprising,
a) separately storing, at least one composition comprising, in a cosmetically acceptable medium,
at least one fluorescent dye that is soluble in the medium, wherein the at least one fluorescent dye is chose from compounds of the following formulae;

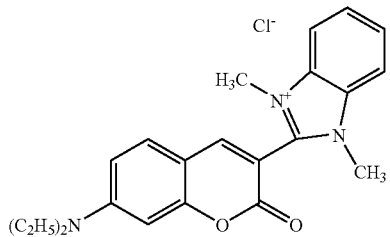

(F1)

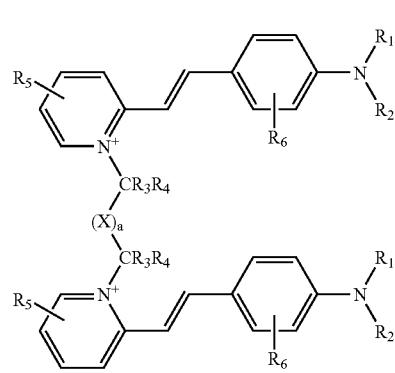

(F3)

wherein:
$R_1$ and $R_2$, which may be identical or different, are each chosen from:
a hydrogen atom;
linear and branched alkyl radicals comprising from 1 to 10 carbon atoms, wherein the alkyl radicals are optionally interrupted with at least one entity chosen from hetero atoms and groups comprising at least one hetero atom and/or optionally substituted with at least one entity chosen from hetero atoms, groups comprising at least one hetero atom, and halogen atoms;
aryl and arylalkyl radicals, wherein the aryl group comprises 6 carbon atoms and the alkyl radical comprises from 1 to 4 carbon atoms; and wherein the aryl radical is optionally substituted with at least one alkyl radical chosen from linear and branched alkyl radicals comprising 1 to 4 carbon atoms optionally interrupted with at least one entity chosen from hetero atoms and groups comprising at least one hetero atom and/or optionally substituted with at least one entity chosen from hetero atoms, groups comprising at least one hetero atom, and halogen atoms;
$R_1$ and $R_2$ may optionally form, together with the nitrogen to which they are attached, a heterocycle and may comprise at least one other hetero atom, wherein the heterocycle is optionally substituted with at least one alkyl radical chosen from linear and branched alkyl radicals, wherein the at least one alkyl radical is optionally interrupted with at least one entity chosen from hetero atoms and groups comprising at least one hetero atom and/or optionally substituted with at least one entity chosen from hetero atoms, groups comprising at least one hetero atom, and halogen atoms;
$R_1$ or $R_2$ may optionally form, together with the nitrogen atom to which they are attached and one of the carbon atoms of the phenyl group bearing the nitrogen atom, a heterocycle;
$R_3$ and $R_4$, which may be identical or different, are each chosen from a hydrogen atom and alkyl radicals comprising from 1 to 4 carbon atoms;
$R_5$, which may be identical or different, is chosen from a hydrogen atom, a halogen atom and linear and branched alkyl radicals comprising from 1 to 4 carbon atoms, optionally interrupted with at least one hetero atom;

$R_6$, which may be identical or different, is chosen from a hydrogen atom; a halogen atom; linear and branched alkyl radicals comprising from 1 to 4 carbon atoms, wherein the alkyl radicals are optionally substituted with at least one entity chosen from hetero atoms, groups bearing at least one hetero atom, and halogen atoms and/or optionally interrupted with at least one entity chosen from hetero atoms and groups bearing at least one hetero atom;

X is chosen from:
linear and branched alkyl radicals comprising from 1 to 14 carbon atoms and alkenyl radicals comprising from 2 to 14 carbon atoms, wherein the alkyl and alkenyl radicals are optionally interrupted with at least one entity chosen from hetero atoms and groups comprising at least one hetero atom and/or optionally substituted with at least one entity chosen from hetero atoms, groups comprising at least one hetero atom, and halogen atoms;

5- and 6-membered heterocyclic radicals optionally substituted with at least one alkyl radical chosen from linear and branched alkyl radicals comprising from 1 to 14 carbon atoms, optionally substituted with at least one entity chosen from hetero atoms; linear and branched aminoalkyl radicals comprising from 1 to 4 carbon atoms, optionally substituted with at least one hetero atom; and halogen atoms;

fused and non-fused aromatic and diaromatic radicals, optionally separated with at least one alkyl radical comprising from 1 to 4 carbon atoms, the at least one aryl aromatic and diaromatic radicals radical is optionally substituted with at least one entity chosen from halogen atoms and alkyl radicals comprising from 1 to 10 carbon atoms optionally substituted and/or interrupted with at least one entity chosen from hetero atoms and groups bearing at least one hetero atom;

a dicarbonyl radical; and wherein the group X possibly bears at least one cationic charge;

a is equal to 0 or 1;

$Y^-$, which may be identical or different, is chosen from organic and mineral anions; and n is an integer equal to at least 2 and at most equal to the number of cationic charges present in the at least one fluorescent dye; and

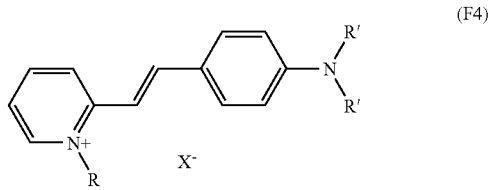

(F4)

wherein R is chosen from methyl and ethyl radicals; R' is a methyl radical and $X^-$ is chosen from anions
and
at least one conditioning agent that is insoluble in the medium, chosen from;
synthetic oils;
mineral oils;
plant oils;
animal oils;
fluoro oils;
perfluoro oils;
natural and synthetic waxes;
carboxylic acid esters; and
compounds of formula $R_3CHOH\text{—}CH(NH\text{-}COR_1)\text{—}CH_2OR_2$, wherein
$R_1$ is chosen from $C_4$–$C_{30}$ alkyl radicals, optionally substituted in at least one position chosen from the α position with at least one hydroxyl radical and the ω position with at least one hydroxyl radical esterified with at least one fatty acid chosen from $C_{16}$–$C_{30}$ fatty acids,
$R_2$ is chosen from a hydrogen atom and (glycosyl)$_n$ and (galactosyl)$_m$ radicals wherein n is a number ranging from 1 to 4 and m is a number ranging from 1 to 8, and
$R_3$ is chosen from $C_{15}$–$C_{26}$ hydrocarbon-based radicals optionally substituted with at least one radical chosen from alkyl radicals and $C_{15}$–$C_{26}$ α-hydroxyalkyl radicals optionally esterified with at least one $C_{16}$–$C_{30}$ α-hydroxy acid and
at least one oxidizing composition comprising, in a cosmetically acceptable medium, at least one oxidizing agent;
b) mixing the at least one composition and the at least one oxidizing composition at the time of use;
c) applying the mixture to the keratin fibers;
d) leaving the mixture on the keratin fibers to act for a time period sufficient to develop the desired coloration; and
e) rinsing the keratin fibers, optionally washing the keratin fibers with shampoo, rinsing the keratin fibers and drying the keratin fibers.

39. The process according to claim 37, wherein the at least one composition is applied to hair with a tone height of less than or equal to 6.

40. The process according to claim 39, wherein the at least one composition is applied to hair with a tone height of less than or equal to 4.

41. The process according to claim 38, wherein the at least one composition is applied to hair with a tone height of less than or equal to 6.

42. The process according to claim 39, wherein the at least one composition is applied to hair with a tone height of less than or equal to 4.

43. The process according to claim 37, wherein the human keratin fibers are artificially colored or pigmented.

44. The process according to claim 38, wherein the human keratin fibers are artificially colored or pigmented.

45. A process for coloring dark skin with a lightening effect comprising,
applying to the skin at least one composition, comprising, in a cosmetically acceptable medium,
at least one fluorescent dye that is soluble in the medium and
at least one conditioning agent that is insoluble in the medium, chosen from;
synthetic oils;
mineral oils;
plant oils;
animal oils;
fluoro oils;
perfluoro oils;
natural and synthetic waxes;
carboxylic acid esters; and
compounds of formula $R_3CHOH\text{—}CH(NH\text{-}COR_1)\text{—}CH_2OR_2$, wherein R₁ is chosen from $C_{14}$–$C_{30}$ alkyl radicals, optionally substituted in at least one position chosen from the α position with at least one hydroxyl radical and the ω position with at least one hydroxyl radical esterified with at least one fatty acid chosen from $C_{16}$–$C_{30}$ fatty acids, R₂ is chosen from a hydrogen atom and (glycosyl)$_n$ and (galactosyl)$_m$ radicals wherein n is a number ranging from 1 to 4 and m is a number ranging from 1 to 8, and R₃ is chosen from $C_{15}$–$C_{26}$ hydrocarbon-based radicals optionally substituted with at least one radical chosen from alkyl radicals and $C_{15}$–$C_{26}$ α-hydroxyalkyl radicals optionally esterified with at least one $C_{16}$–$C_{30}$ α-hydroxy acid and drying the skin or leaving the skin to dry.

46. A multi-compartment device for dyeing and lightening keratin fibers, comprising,
at least one compartment comprising at least one composition, comprising, in a cosmetically acceptable medium,
at least one fluorescent dye that is soluble in the medium, wherein the at least one fluorescent dye is chose from compounds of the following formulae:

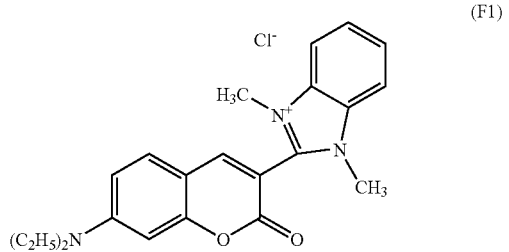

(F1)

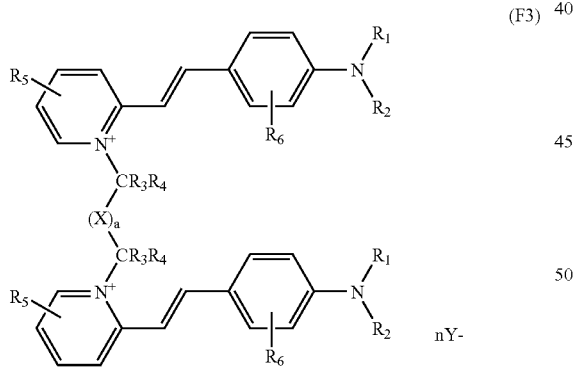

(F3)

wherein;

R₁ and R₂, which may be identical or different, are each chosen from:
a hydrogen atom;
linear and branched alkyl radicals comprising from 1 to 10 carbon atoms, wherein the alkyl radicals are optionally interrupted with at least one entity chosen from hetero atoms and groups comprising at least one hetero atom and/or optionally substituted with at least one entity chosen from hetero atoms, groups comprising at least one hetero atom, and halogen atoms;

aryl and arylalkyl radicals, wherein the aryl group comprises 6 carbon atoms and the alkyl radical comprises from 1 to 4 carbon atoms; and wherein the aryl radical is optionally substituted with at least one alkyl radical chosen from linear and branched alkyl radicals comprising 1 to 4 carbon atoms optionally interrupted with at least one entity chosen from hetero atoms and groups comprising at least one hetero atom and/or optionally substituted with at least one entity chosen from hetero atoms, groups comprising at least one hetero atom, and halogen atoms;

R₁ and R₂ may optionally form, together with the nitrogen to which they are attached, a heterocycle and may comprise at least one other hetero atom, wherein the heterocycle is optionally substituted with at least one alkyl radical chosen from linear and branched alkyl radicals, wherein the at least one alkyl radical is optionally interrupted with at least one entity chosen from hetero atoms and groups comprising at least one hetero atom and/or optionally substituted with at least one entity chosen from hetero atoms, groups comprising at least one hetero atom, and halogen atoms;

R₁ or R₂ may optionally form, together with the nitrogen atom to which they are attached and one of the carbon atoms of the phenyl group bearing the nitrogen atom, a heterocycle;

R₃ and R₄, which may be identical or different, are each chosen from a hydrogen atom and alkyl radicals comprising from 1 to 4 carbon atoms;

R₅, which may be identical or different, is chosen from a hydrogen atom, a halogen atom and linear and branched alkyl radicals comprising from 1 to 4 carbon atoms, optionally interrupted with at least one hetero atom;

R₆, which may be identical or different, is chosen from a hydrogen atom; a halogen atom; linear and branched alkyl radicals comprising from 1 to 4 carbon atoms, wherein the alkyl radicals are optionally substituted with at least one entity chosen from hetero atoms, groups bearing at least one hetero atom, and halogen atoms and/or optionally interrupted with at least one entity chosen from hetero atoms and groups bearing at least one hetero atom;

X is chosen from;
linear and branched alkyl radicals comprising from 1 to 14 carbon atoms and alkenyl radicals comprising from 2 to 14 carbon atoms, wherein the alkyl and alkenyl radicals are optionally interrupted with at least one entity chosen from hetero atoms and groups comprising at least one hetero atom and/or optionally substituted with at least one entity chosen from hetero atoms, groups comprising at least one hetero atom, and halogen atoms;
5- and 6-membered heterocyclic radicals optionally substituted with at least one alkyl radical chosen from linear and branched alkyl radicals comprising from 1 to 14 carbon atoms, optionally substituted with at least one entity chosen from hetero atoms; linear and branched aminoalkyl radicals comprising from 1 to 4 carbon atoms, optionally substituted with at least one hetero atom; and halogen atoms;
fused and non-fused aromatic and diaromatic radicals, optionally separated with at least one alkyl radical comprising from 1 to 4 carbon atoms, the at least one aryl aromatic and diaromatic radicals radical is optionally substituted with at least one entity chosen from halogen atoms and alkyl radicals comprising from 1 to 10 carbon atoms optionally substituted and/or interrupted with at least one entity chosen from hetero atoms and groups bearing at least one hetero atom;

a dicarbonyl radical; and wherein the group X possibly bears at least one cationic charge;

a is equal to 0 or 1;

$Y^-$, which may be identical or different, is chosen from organic and mineral anions; and n is an integer equal to at least 2 and at most equal to the number of cationic charges present in the at least one fluorescent dye; and (F4)

wherein R is chosen from methyl and ethyl radicals; R' is a methyl radical and $X^-$ is chosen from anions
and
at least one conditioning agent that is insoluble in the medium, chosen from:
synthetic oils;
mineral oils;
plant oils;
animal oils;
fluoro oils;
perfluoro oils;
natural and synthetic waxes;
carboxylic acid esters; and
compounds of formula $R_3CHOH$—$CH(NH$-$COR_1)$—$CH_2OR_2$, wherein
$R_1$ is chosen from $C_{14}$–$C_{30}$ alkyl radicals, optionally substituted in at least one position chosen from the α position with at least one hydroxyl radical and the ω position with at least one hydroxyl radical esterified with at least one fatty acid chosen from $C_{16}$–$C_{30}$ fatty acids,
$R_2$ is chosen from a hydrogen atom and (glycosyl)$_n$ and (galactosyl)$_m$ radicals wherein n is a number ranging from 1 to 4 and m is a number ranging from 1 to 8, and
$R_3$ is chosen from $C_{15}$–$C_{26}$ hydrocarbon-based radicals optionally substituted with at least one radical chosen from alkyl radicals and $C_{15}$–$C_{26}$ α-hydroxyalkyl radicals optionally esterified with at least one $C_{16}$–$C_{30}$ α-hydroxy acid and
at least one other compartment comprising at least one oxidizing composition comprising at least one oxidizing agent.

47. A method for coloring a keratin material with a lightening effect comprising applying, at least one composition, comprising, in a cosmetically acceptable medium,
at least one fluorescent dye that is soluble in the medium, wherein the at least one fluorescent dye is chose from compounds of the following formulae:

(F1)

(F3)

wherein:
$R_1$ and $R_2$, which may be identical or different, are each chosen from:
a hydrogen atom;
linear and branched alkyl radicals comprising from 1 to 10 carbon atoms, wherein the alkyl radicals are optionally interrupted with at least one entity chosen from hetero atoms and groups comprising at least one hetero atom and/or optionally substituted with at least one entity chosen from hetero atoms, groups comprising at least one hetero atom, and halogen atoms;
aryl and arylalkyl radicals, wherein the aryl group comprises 6 carbon atoms and the alkyl radical comprises from 1 to 4 carbon atoms; and wherein the aryl radical is optionally substituted with at least one alkyl radical chosen from linear and branched alkyl radicals comprising 1 to 4 carbon atoms optionally interrupted with at least one entity chosen from hetero atoms and groups comprising at least one hetero atom and/or optionally substituted with at least one entity chosen from hetero atoms, groups comprising at least one hetero atom, and halogen atoms;
$R_1$ and $R_2$, may optionally form, together with the nitrogen to which they are attached, a heterocycle and may comprise at least one other hetero atom, wherein the heterocycle is optionally substituted with at least one alkyl radical chosen from linear and branched alkyl radicals, wherein the at least one alkyl radical is optionally interrupted with at least one entity chosen from hetero atoms and groups comprising at least one hetero atom and/or optionally substituted with at least one entity chosen from hetero atoms, groups comprising at least one hetero atom, and halogen atoms;

R₁ or R₂ may optionally form, together with the nitrogen atom to which they are attached and one of the carbon atoms of the phenyl group bearing the nitrogen atom, a heterocycle;

R₃ and R₄, which may be identical or different, are each chosen from a hydrogen atom and alkyl radicals comprising from 1 to 4 carbon atoms;

R₅, which may be identical or different, is chosen from a hydrogen atom, a halogen atom and linear and branched alkyl radicals comprising from 1 to 4 carbon atoms, optionally interrupted with at least one hetero atom;

R₆, which may be identical or different, is chosen from a hydrogen atom; a halogen atom; linear and branched alkyl radicals comprising from 1 to 4 carbon atoms, wherein the alkyl radicals are optionally substituted with at least one entity chosen from hetero atoms, groups bearing at least one hetero atom, and halogen atoms and/or optionally interrupted with at least one entity chosen from hetero atoms and groups bearing at least one hetero atom;

X is chosen from:
  linear and branched alkyl radicals comprising from 1 to 14 carbon atoms and alkenyl radicals comprising from 2 to 14 carbon atoms, wherein the alkyl and alkenyl radicals are optionally interrupted with at least one entity chosen from hetero atoms and groups comprising at least one hetero atom and/or optionally substituted with at least one entity chosen from hetero atoms, groups comprising at least one hetero atom, and halogen atoms;
  5- and 6-membered heterocyclic radicals optionally substituted with at least one alkyl radical chosen from linear and branched alkyl radicals comprising from 1 to 14 carbon atoms, optionally substituted with at least one entity chosen from hetero atoms; linear and branched aminoalkyl radicals comprising from 1 to 4 carbon atoms, optionally substituted with at least one hetero atom; and halogen atoms;
  fused and non-fused aromatic and diaromatic radicals, optionally separated with at least one alkyl radical comprising from 1 to 4 carbon atoms, the at least one aryl aromatic and diaromatic radicals radical is optionally substituted with at least one entity chosen from halogen atoms and alkyl radicals comprising from 1 to 10 carbon atoms optionally substituted and/or interrupted with at least one entity chosen from hetero atoms and groups bearing at least one hetero atom;
  a dicarbonyl radical; and
  wherein the group X possibly bears at least one cationic charge;

a is equal to 0 or 1;

Y⁻, which may be identical or different, is chosen from organic and mineral anions; and n is an integer equal to at least 2 and at most equal to the number of cationic charges present in the at least one fluorescent dye; and

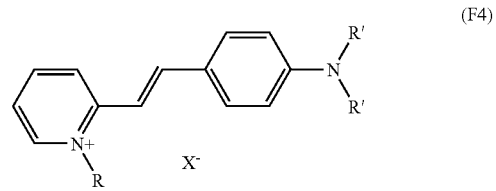

(F4)

wherein R is chosen from methyl and ethyl radicals; R' is a methyl radical and X⁻ is chosen from anions
and
  at least one conditioning agent that is insoluble in the medium, chosen from:
    synthetic oils;
    mineral oils;
    plant oils;
    animal oils;
    fluoro oils;
    perfluoro oils;
    natural and synthetic waxes;
    carboxylic acid esters; and
    compounds of formula R₃CHOH—CH(NH-COR₁)—CH₂OR₂, wherein
      R₁ is chosen from C₁₄–C₃₀ alkyl radicals, optionally substituted in at least one position chosen from the α position with at least one hydroxyl radical and the ω position with at least one hydroxyl radical esterified with at least one fatty acid chosen from C₁₆–C₃₀ fatty acids,
      R₂ is chosen from a hydrogen atom and (glycosyl)n and (galactosyl)m radicals wherein n is a number ranging from 1 to 4 and m is a number ranging from 1 to 8, and
      R₃ is chosen from C₁₅–C₂₆ hydrocarbon-based radicals optionally substituted with at least one radical chosen from alkyl radicals and C₁₅–C₂₆ α-hydroxyalkyl radicals optionally esterified with at least one C₁₆–C₃₀ α-hydroxy acid.

48. The method according to claim 47, wherein the keratin material is artificially colored or pigmented keratin fibers.

49. The method according to claim 48, wherein the keratin material is hair and/or dark skin.

50. The method according to claim 47, wherein the hair has a tone height of less than or equal to 6.

51. The method according to claim 50, wherein the hair has a tone height of less than or equal to 4.

* * * * *

UNITED STATES PATENT AND TRADEMARK OFFICE
CERTIFICATE OF CORRECTION

PATENT NO. : 7,150,764 B2
APPLICATION NO. : 10/814337
DATED : December 19, 2006
INVENTOR(S) : Grégory Plos et al.

It is certified that error appears in the above-identified patent and that said Letters Patent is hereby corrected as shown below:

Claim 1, column 25, line 66, replace "chose" with -- chosen --.

Claim 37, column 31, line 9, replace "chose" with -- chosen --.

Claim 37, column 32, line 63, replace "$Y\_$" with -- $Y^-$ --.

Claim 38, column 33, line 54, replace "chose" with -- chosen --.

Claim 47, column 39, line 66, replace "chose" with -- chosen --.

Signed and Sealed this

Third Day of April, 2007

JON W. DUDAS
*Director of the United States Patent and Trademark Office*